US012636001B1

(12) United States Patent
Ix et al.

(10) Patent No.: US 12,636,001 B1
(45) Date of Patent: May 26, 2026

(54) ANKLE REPLACEMENT DISTRACTOR SYSTEMS AND METHODS

(71) Applicant: Advita Ortho LLC, Gainesville, FL (US)

(72) Inventors: Ian Ix, Gainesville, FL (US); Michael Mauldin, Gainesville, FL (US); Aldo Moreno-Reyes, Gainesville, FL (US); James Nunley, Durham, NC (US); Mark Easley, Durham, NC (US); James DeOrio, Durham, NC (US)

(73) Assignee: Advita Ortho, LLC, Gainesville, FL (US)

( * ) Notice: Subject to any disclaimer, the term of this patent is extended or adjusted under 35 U.S.C. 154(b) by 0 days.

(21) Appl. No.: 19/326,517

(22) Filed: Sep. 11, 2025

(51) Int. Cl.
| | |
|---|---|
| *A61B 17/02* | (2006.01) |
| *A61B 17/56* | (2006.01) |
| *A61B 90/00* | (2016.01) |
| *A61F 2/42* | (2006.01) |
| *A61F 2/46* | (2006.01) |
| *A61B 17/00* | (2006.01) |
| *A61F 2/30* | (2006.01) |

(52) U.S. Cl.
CPC ............ *A61B 17/025* (2013.01); *A61B 17/56* (2013.01); *A61B 90/08* (2016.02); *A61F 2/4202* (2013.01); *A61F 2/4606* (2013.01); *A61B 2017/00407* (2013.01); *A61B 2017/564* (2013.01); *A61B 2090/0807* (2016.02); *A61F 2002/30205* (2013.01); *A61F 2002/30535* (2013.01); *A61F 2002/4205* (2013.01); *A61F 2002/4628* (2013.01)

(58) Field of Classification Search
CPC .................................................... A61B 17/025
See application file for complete search history.

(56) References Cited

U.S. PATENT DOCUMENTS

| | | | | |
|---|---|---|---|---|
| 3,486,505 A | * | 12/1969 | Morrison | ............. A61B 17/025 606/86 A |
| 3,840,014 A | * | 10/1974 | Ling | .................... A61B 17/025 606/90 |

(Continued)

FOREIGN PATENT DOCUMENTS

WO        2025/174764 A1      8/2025

*Primary Examiner* — Christian A Sevilla
(74) *Attorney, Agent, or Firm* — GREENBERG TRAURIG, LLP

(57) ABSTRACT

A surgical system for joint procedures includes a distractor device with two pivotable arms and two distracting members, along with two attachable tools—one designed to hold or position a prosthetic device and interface with a bone surface, and the other to interface with the opposing bone surface and allow passage of the prosthetic device. The distractor device adjusts the arms to move closer together or farther apart, modifying the space between bone surfaces. The first tool securely engages a prosthetic device or interfaces with a bone. The second tool fits the opposing bone and includes an opening for the prosthetic device to pass through. This system facilitates controlled joint distraction and precise insertion and alignment of a prosthetic device, such as a stemmed tibial implant, during orthopedic surgery. The system is beneficial for procedures like total ankle replacement, enhancing surgical access and outcomes by supporting accurate placement of implants.

20 Claims, 34 Drawing Sheets

(56) References Cited

U.S. PATENT DOCUMENTS

| | | | |
|---|---|---|---|
| 4,050,464 A * | 9/1977 | Hall ..................... | A61B 17/025 |
| | | | 606/103 |
| 5,586,564 A * | 12/1996 | Barrett ................. | A61B 17/025 |
| | | | 606/167 |
| 10,357,236 B2 | 7/2019 | De Mayo et al. | |
| 11,154,289 B2 | 10/2021 | Schussler | |
| 2007/0100212 A1 * | 5/2007 | Pimenta ............. | A61B 17/0218 |
| | | | 600/210 |
| 2025/0288305 A1 | 9/2025 | Dalton et al. | |

* cited by examiner

Section AA

Section BB

Section DD

Section EE

ANKLE REPLACEMENT DISTRACTOR SYSTEMS AND METHODS

FIELD OF THE INVENTION

The field of invention relates to orthopedic surgery. More particularly, the field of invention relates to distractor devices that facilitate the insertion of prosthetic implants, and to methods for use of such devices.

BACKGROUND OF THE INVENTION

Total ankle replacement procedures require precise preparation of joint surfaces and accurate placement of implants within a limited operative space. Existing distractor devices often occupy substantial volume in the anterior corridor, restricting access and complicating insertion of larger stemmed tibial components.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

SUMMARY OF THE DISCLOSURE

Figure 1:
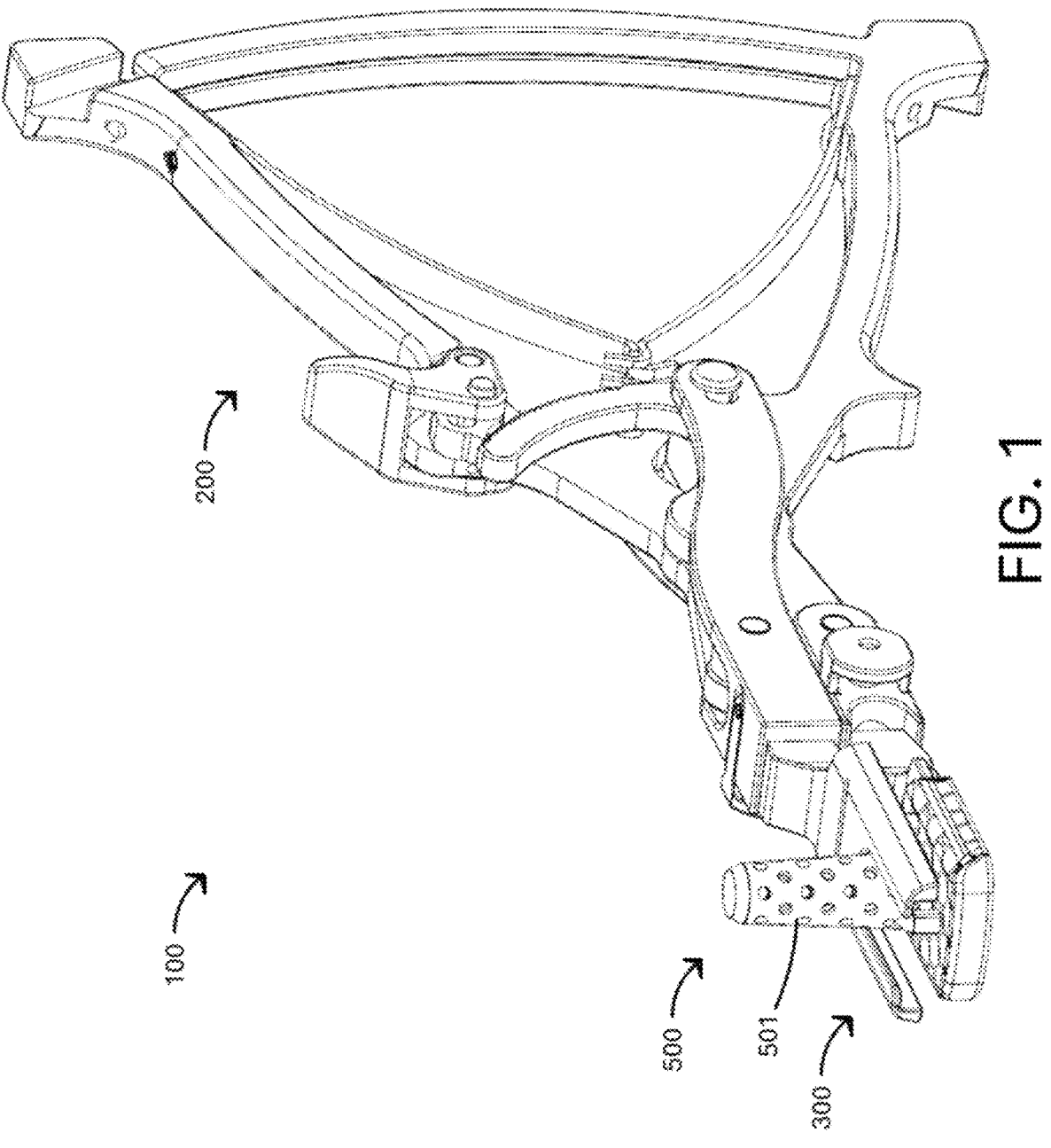
FIG. 1 illustrates an embodiment of a distractor system including detachable tools, the distractor system shown in use with a stemmed tibial implant.

In some embodiments, a system includes a distractor device, a first tool, and a second tool, the distractor device including a first engageable arm that is configured to be engaged by a user; a second engageable arm that is configured to be engaged by a user, wherein the first engageable arm is pivotably connected to the second arm; a first distracting member that is coupled to the first engageable arm and to the second engageable arm; a second distracting member that is coupled to the first engageable arm and to the second engageable arm; wherein the first engageable arm, the second engageable arm, the first distracting member, and the second distracting member are operably coupled to one another such that: pivotable motion of the first engageable arm toward the second engageable arm causes the first distracting member and the second distracting member to move away from one another, and pivotable motion of the first engageable arm away from the second engageable arm causes the first distracting member and the second distracting member to move toward one another; the first tool having a first end, a second end, a planar surface, and a retention mechanism, wherein the second end of the first tool is configured to releasably engage a prosthetic device, wherein the retention mechanism is configured to retain the second end of the first tool in engagement with prosthetic device, wherein at least one of: (a) the planar surface is configured to interface with a first bony surface of two opposing bony surfaces of a joint of a patient, or (b) the first tool is configured to position the prosthetic device to interface with the first bony surface, and wherein the first end of the first tool is one of (a) configured to be detachably coupled to the second end of the first distracting member, or (b) integrally formed with the second end of the first distracting member; and the second tool a second tool having a first end, a second end, and a planar surface, wherein the planar surface of the second tool is configured to interface with a second bony surface of the two opposing bony surfaces, wherein the second tool defines at least one void, wherein the void is sufficiently, shaped, and positioned such that, when (a) the first tool is assembled to the first distracting member, (b) the second tool is assembled to the second distracting member, and (c) the prosthetic device is coupled to the first tool, at least a portion of the prosthetic device passes through the at least one void, and wherein the first end of the second tool is one of (a) configured to be detachably coupled to the second end of the second distracting member, or (b) integrally formed with the second end of the second detaching member.

In some embodiments, the distractor device also includes a transverse arm, wherein the transverse arm includes indicators positioned so as to indicate a distance between the first distracting member and the second distracting member, and wherein the transverse arm is positioned on one of the first engageable arm or the second engageable arm. In some embodiments, the indicators include one of laser markings or etchings.

In some embodiments, the distractor device also includes a locking mechanism operable to releasably lock the distractor device, wherein, when the distractor device is locked, the first distracting member and the second distracting member are prevented from moving toward one another. In some embodiments, the locking mechanism includes a releasable ratcheting mechanism connecting the first engageable arm to the second engageable arm. In some embodiments, the releasable ratcheting mechanism includes: teeth on one of the first engageable arm or the second engageable arm, and a pawl on an other one of the first engageable arm or the second engageable arm. In some embodiments, the releasable ratcheting mechanism also includes a spring-loaded latch operable by a user to release the pawl.

In some embodiments, the first end of the first tool is one of configured to be detachably coupled to the second end of the second distracting member, the first distracting member includes a female pocket configured to releasably retain the first tool, the first end of the second tool is configured to be detachably coupled to the second end of the second distracting member, and the second distracting member includes a female pocket configured to releasably retain the second tool. In some embodiments, each of the female pockets includes a hole configured to receive the first end one of the first tool or the second tool, and a biasing member for retaining the first end of the one of the first tool or the second tool within the hole.

In some embodiments, the first end of the second tool and the second end of the second tool define a length axis, the second tool has a length as measured along the length axis, the second tool has a width as measured transverse to the length axis, and the length is greater than the width. In some embodiments, the void is outlined along the length axis of the second tool leading away from the second end of the second tool.

In some embodiments, the retention mechanism includes a flexure configured to interface with the prosthetic device.

In some embodiments, the prosthetic device includes a stemmed tibial implant for a total ankle replacement.

In some embodiments, a method includes forming an anterior resection of a first bone of a joint of a patient to form a space between the first bone and a second bone of the joint; forming a stem hole in a distal end of the first bone; attaching a first tool to a first distracting member of a distractor device, wherein the distractor device includes: a first engageable arm that is configured to be engaged by a user; a second engageable arm that is configured to be engaged by a user, wherein the first engageable arm is pivotably connected to the second arm; a first distracting member that is coupled to the first engageable arm and to the second engageable arm; a second distracting member that is coupled to the first engageable arm and to the second engageable arm; wherein the first engageable arm, the second engageable arm, the first distracting member, and the second distracting member are operably coupled to one another such that: pivotable motion of the first engageable arm toward the second engageable arm causes the first distracting member and the second distracting member to move away from one another, and pivotable motion of the first engageable arm away from the second engageable arm causes the first distracting member and the second distracting member to move toward one another; wherein the first tool has a first end, a second end, a planar surface, and a retention mechanism, wherein the second end of the first tool is configured to releasably engage a prosthetic device, wherein the retention mechanism is configured to retain the second end of the first tool in engagement with prosthetic device, wherein at least one of: (a) the planar surface is configured to interface with a first bony surface of two opposing bony surfaces of a joint of a patient, or (b) the first tool is configured to position the prosthetic device to interface with the first bony surface, and wherein the first end of the first tool is one of (a) configured to be detachably coupled to the second end of the first distracting member, or (b) integrally formed with the second end of the first distracting member; the method also including attaching a second tool to the second distracting member of the distraction device, wherein the second tool has a first end, a second end, and a planar surface, wherein the planar surface of the second tool is configured to interface with a second bony surface of the two opposing bony surfaces, wherein the second tool defines at least one void, wherein the void is sufficiently, shaped, and positioned such that, when (a) the first tool is assembled to the first distracting member, (b) the second tool is assembled to the second distracting member, and (c) the prosthetic device is coupled to the first tool, at least a portion of the prosthetic device passes through the at least one void, and wherein the first end of the second tool is one of (a) configured to be detachably coupled to the second end of the second distracting member, or (b) integrally formed with the second end of the second detaching member; the method also including attaching a prosthetic device to the first tool, wherein the prosthetic device includes a stem; the method also including inserting the distraction device into the space; the method also including operating the distraction device to increase a distance between the first bone and the second bone; the method also including inserting the distraction device further into the space to align the stem of the prosthetic device with the stem hole; and the method also including operating the distraction device to decrease the distance between the first bone and the second bone, so as to result in the stem of the prosthetic device passing through the void of the second tool and into the stem hole.

In some embodiments, the step of forming the stem hole is performed using a cutting bit.

In some embodiments, the method also includes forming peripheral holes around the stem hole using a cutting pin. In some embodiments, the prosthetic device includes peripheral fixation pegs positioned around the stem, and the step of operating the distraction device to decrease the distance between the first bone and the second bone also results in the peripheral fixation pegs passing into the peripheral holes. In some embodiments, the method also includes impacting the prosthetic device so as to fix the stem in the stem hole and so as to fix the peripheral fixation pegs in the peripheral holes. In some embodiments, the step of impacting the prosthetic device is performed using an offset impactor.

In some embodiments, the stem includes a conical cage.

DETAILED DESCRIPTION OF THE DRAWINGS

The following detailed description provides illustrative embodiments of the present technology, which relates generally to surgical instruments, systems, and methods for facilitating joint procedures, particularly in the context of total ankle replacement surgeries. The described technology pertains to a distractor system and associated methods for creating and maintaining surgical space between two bony surfaces to enable the insertion of prosthetic devices or other non-anatomic bodies. While the embodiments described herein are presented in the context of orthopedic applications, the principles of the described technology may be applicable to other surgical fields where joint distraction or precise implant placement is required.

The examples and embodiments described herein are provided for illustrative purposes only and are not intended to limit the scope of the described subject matter. Those skilled in the art will recognize that certain details, such as standard surgical techniques or well-known mechanical principles, may be omitted for clarity and brevity. Furthermore, various modifications, substitutions, and rearrangements of the components or steps described herein may be made without departing from the spirit and scope of the described subject matter, as defined by the appended claims.

As used herein, the term anterior approach refers to a surgical approach to the ankle joint that involves accessing the joint from the front (anterior side) of the body, providing direct access to the tibia and talus without disturbing other bony structures such as the fibula.

As used herein, the term articular surfaces refers to the surfaces of bones that come into contact at a joint, covered with cartilage to facilitate smooth movement.

As used herein, the term bone-on-bone articulation refers to a condition where cartilage between two bones is lost, causing the bones to rub directly against each other, often leading to pain and joint deformity.

As used herein, the term broach refers to a surgical tool used to prepare bone by creating holes or channels, often for the insertion of implants or fixation devices.

As used herein, the term conical central cage refers to a conical-shaped fixation feature of a stemmed tibial implant designed to be inserted into a prepared intramedullary canal for stability and alignment.

As used herein, the term detachable tool refers to a modular component of the distractor system that can be attached or removed from the distracting members, and is configured to interface with bony surfaces or prosthetic devices.

As used herein, the term distracting members refers to components of the distractor system that are pivotably connected to the engageable arms and are responsible for creating separation between two bony surfaces.

As used herein, the term distractor system refers to a surgical instrument designed to create and maintain space between two bony surfaces, such as the tibia and talus, to facilitate the insertion of prosthetic implants or other non-anatomic bodies.

As used herein, the term engageable arms refers to the user-operable arms of the distractor system that are pivotably connected and manipulated to control the movement of the distracting members.

As used herein, the term flexure refers to a flexible component, such as a spring or similar mechanism, used to provide retention or resistance, often to prevent unintended disassembly of components.

As used herein, the term intramedullary canal refers to the central cavity within a bone, such as the tibia, that can be prepared to receive an implant or fixation device.

As used herein, the term joint space refers to the space between two opposing bony surfaces in a joint, such as the tibia and talus in the ankle, which can be manipulated during surgery to allow for implant placement.

As used herein, the term lamina distractor refers to a type of generic orthopedic instrument with scissor-like motion, commonly used to apply distracting forces to separate bony surfaces.

As used herein, the term leaf-spring refers to a mechanically elastic component used in the distractor system to apply a distracting force between the engageable arms, facilitating the separation of bony surfaces.

As used herein, the term non-anatomic body refers to a prosthetic device or implant that is not a natural part of the body, such as a stemmed tibial implant, used to restore function or replace damaged structures.

As used herein, the term peripheral fixation pegs refers to protrusions on a stemmed tibial implant designed to be inserted into prepared peripheral holes in the bone for additional stability.

As used herein, the term pivotable members refers to components of the distractor system that are pivotably connected to each other and to the distracting members, enabling controlled movement and separation of bony surfaces.

As used herein, the term planar surface refers to a flat surface on a detachable tool designed to interface with a bony surface or prosthetic device.

As used herein, the term locking mechanism refers to a releasable ratcheting mechanism in the distractor system that temporarily locks the position of the distracting members to maintain the desired joint space.

As used herein, the term resection refers to the surgical removal of a portion of bone or tissue, often performed to prepare a joint for the insertion of an implant.

As used herein, the term stemmed tibial implant refers to a prosthetic device with a stem that is inserted into the prepared intramedullary canal of the tibia during a total ankle replacement procedure.

As used herein, the term transverse arm refers to a component of the engageable arms that includes indicators for evaluating the distance between the distracting members, aiding in the assessment of joint space and implant compatibility.

As used herein, the term void refers to an opening or cavity in a detachable tool that allows for clearance of a prosthetic device or other non-anatomic body during surgical procedures.

Figure 11:
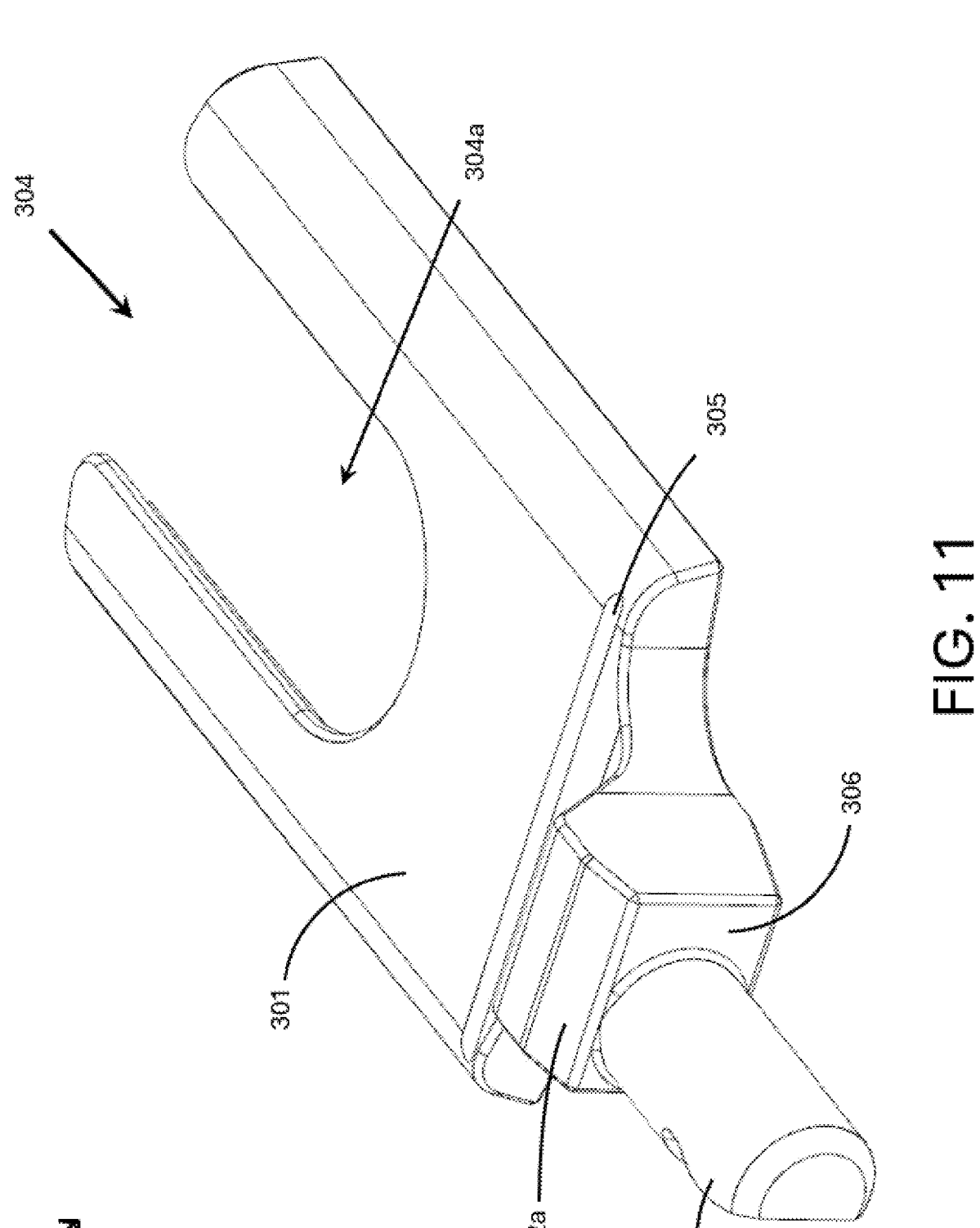
FIG. 11 illustrates a perspective view of an embodiment of a detachable tool conFIG.d for use with the distractor device shown in FIG. 3.
Figure 12:
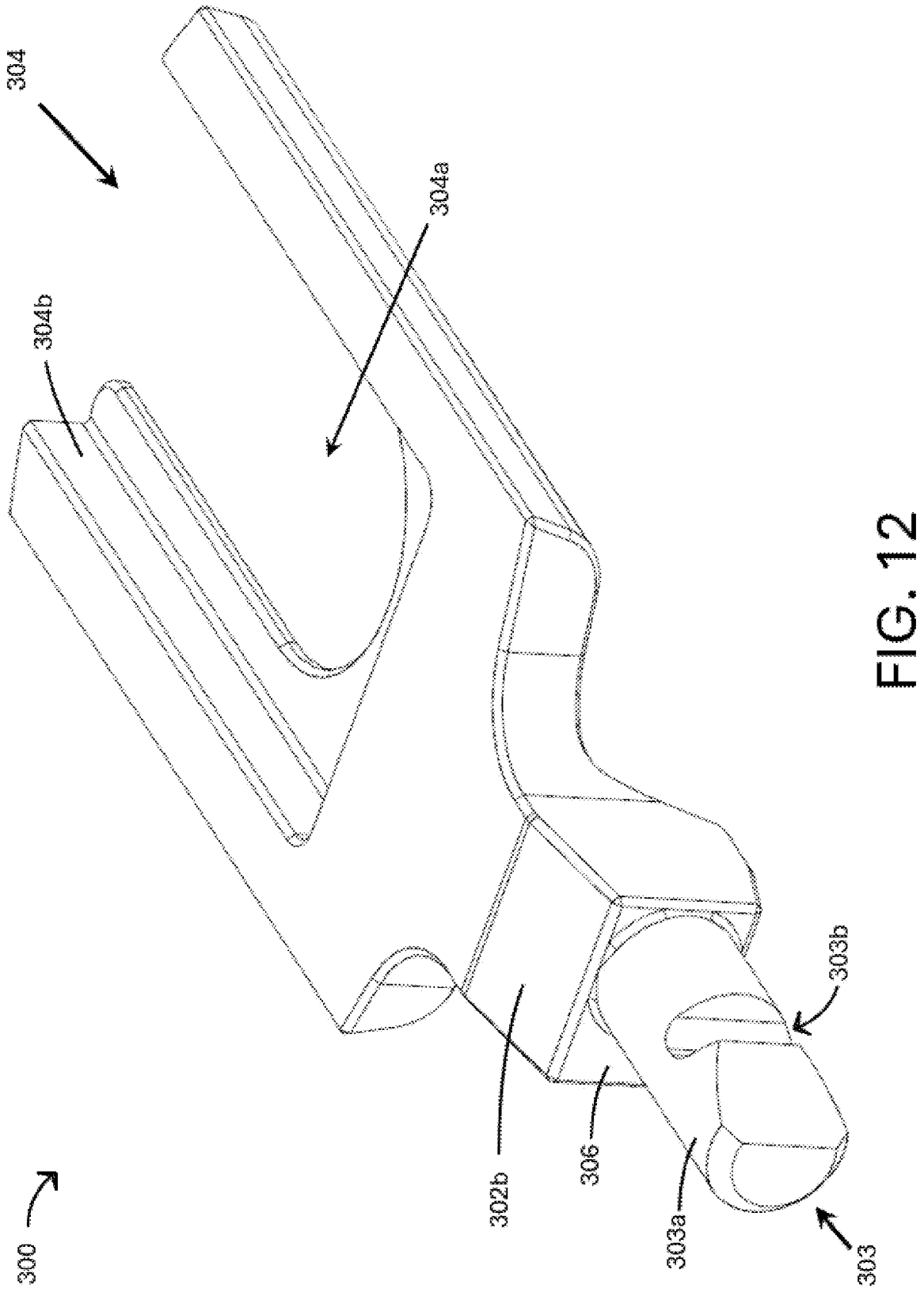
FIG. 12 shows a bottom perspective view of the exemplary detachable tool shown in FIG. 11.
Figures 13, 14:
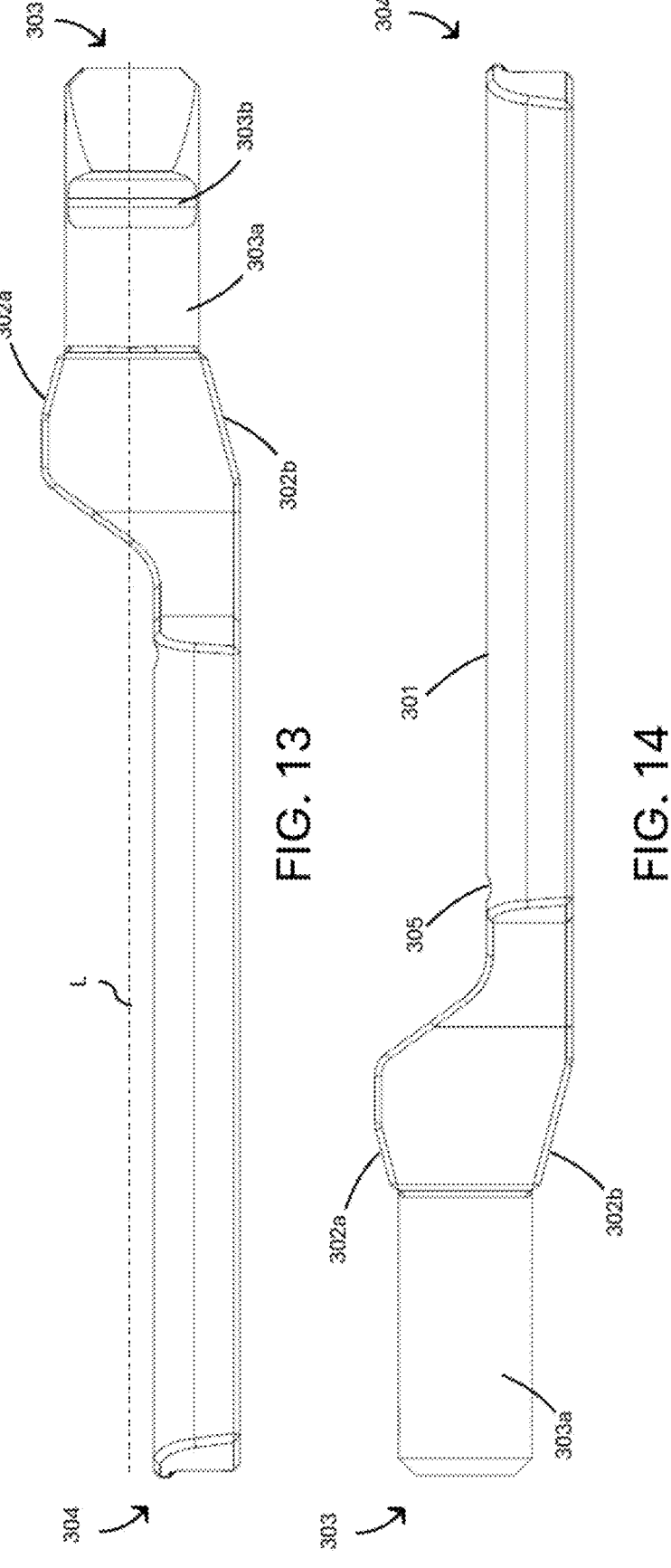
FIG. 13 shows a left side view of the exemplary detachable tool shown in FIG. 11.
FIG. 14 shows a right side view of the exemplary detachable tool shown in FIG. 11.
Figures 15, 16:
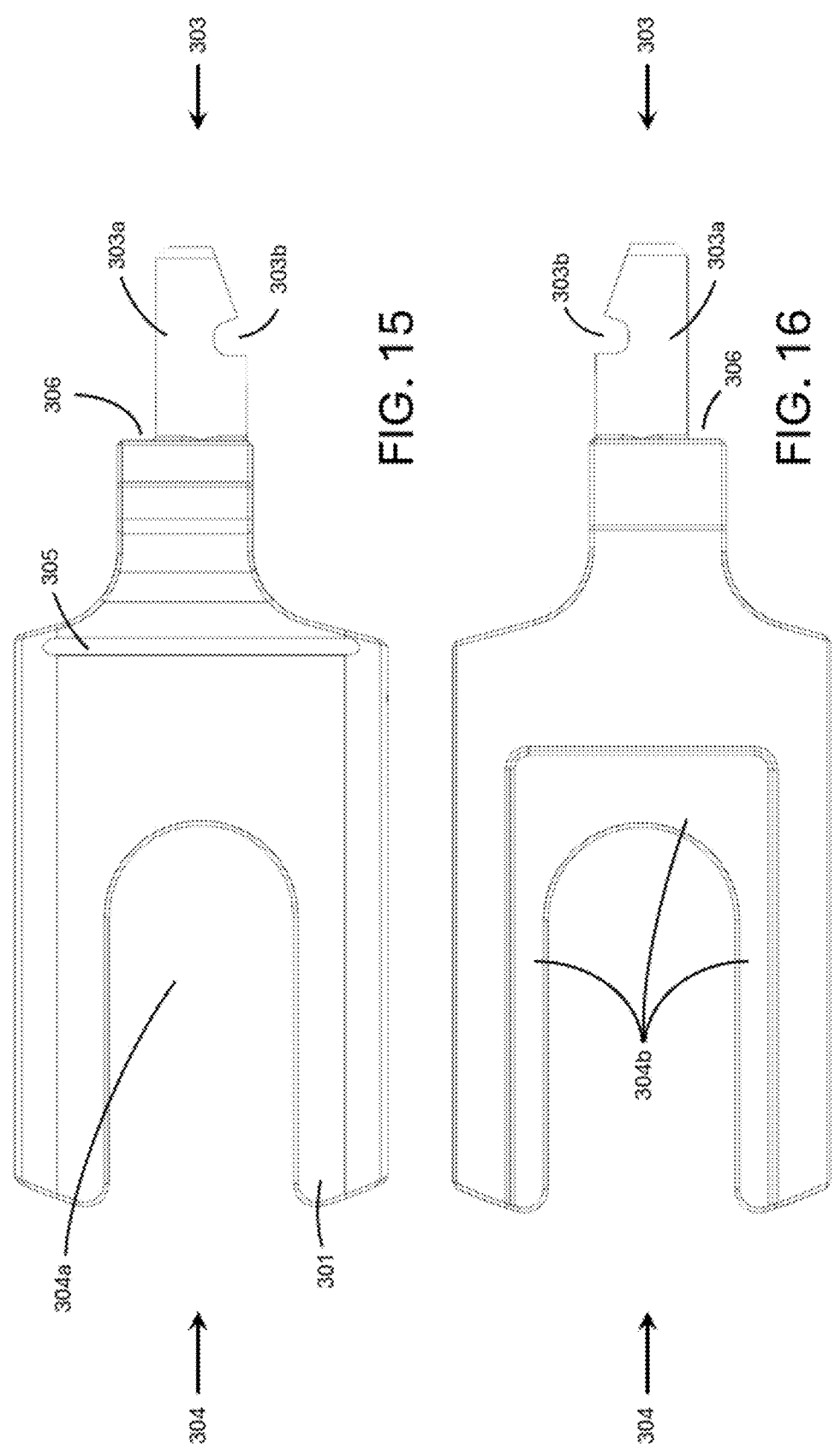
FIG. 15 shows a top view of the exemplary detachable tool shown in FIG. 11.
FIG. 16 shows a perspective view of the exemplary detachable tool shown in FIG. 11.
Figures 17, 18:
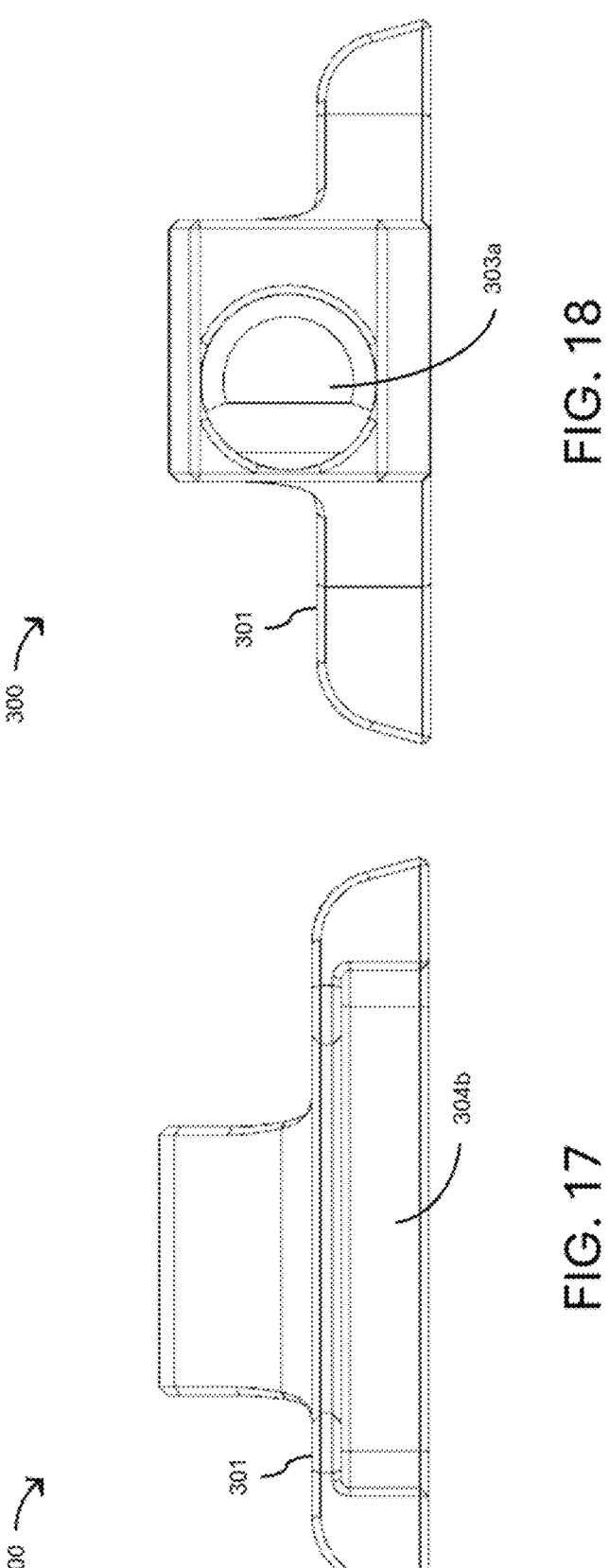
FIG. 17 shows a front view of the exemplary detachable tool shown in FIG. 11.
FIG. 18 shows a rear view of the exemplary detachable tool shown in FIG. 11.
Figure 19:
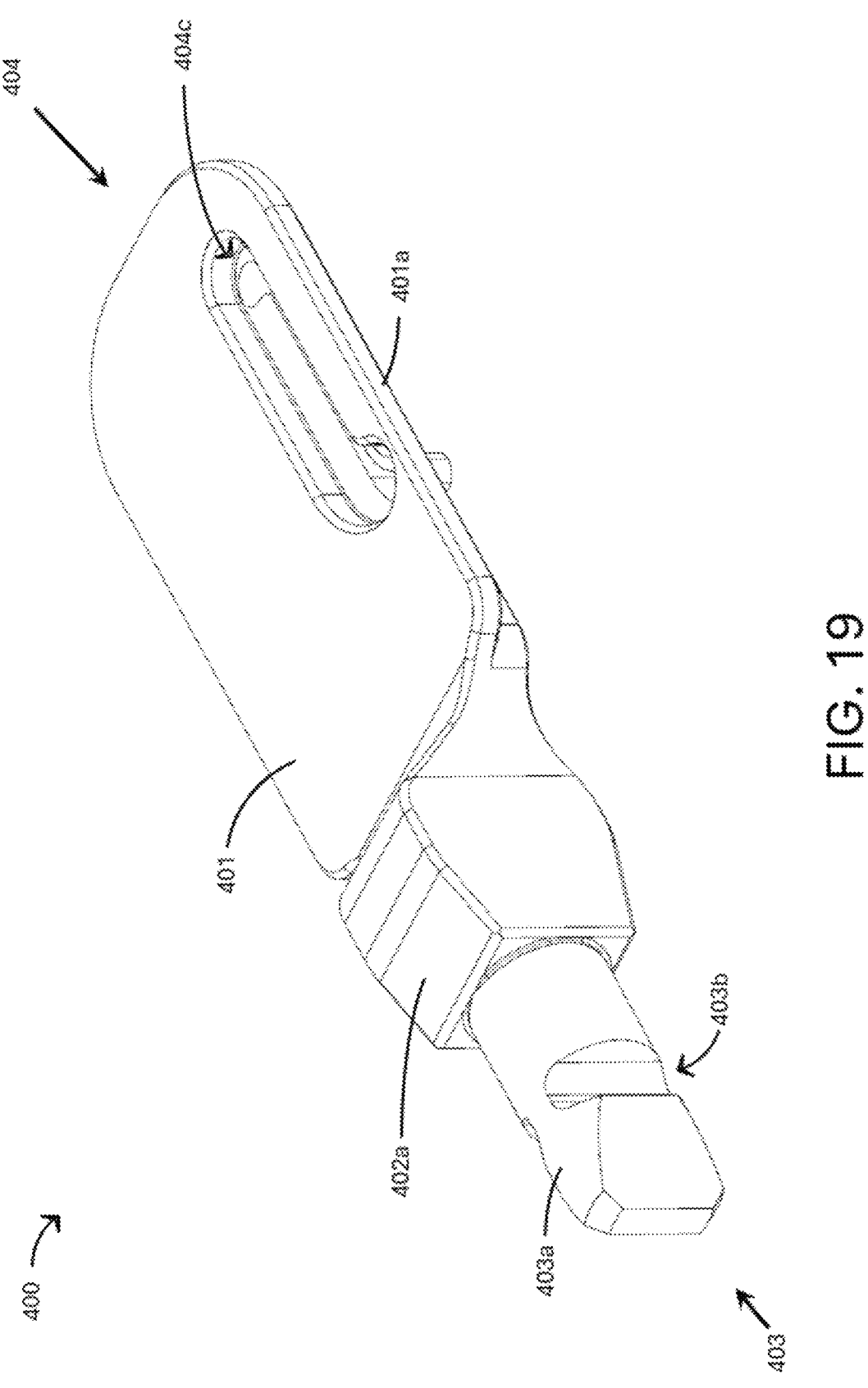
FIG. 19 illustrates a perspective view of an embodiment of a detachable tool conFIG.d for use with the distractor device shown in FIG. 3.
Figure 20:
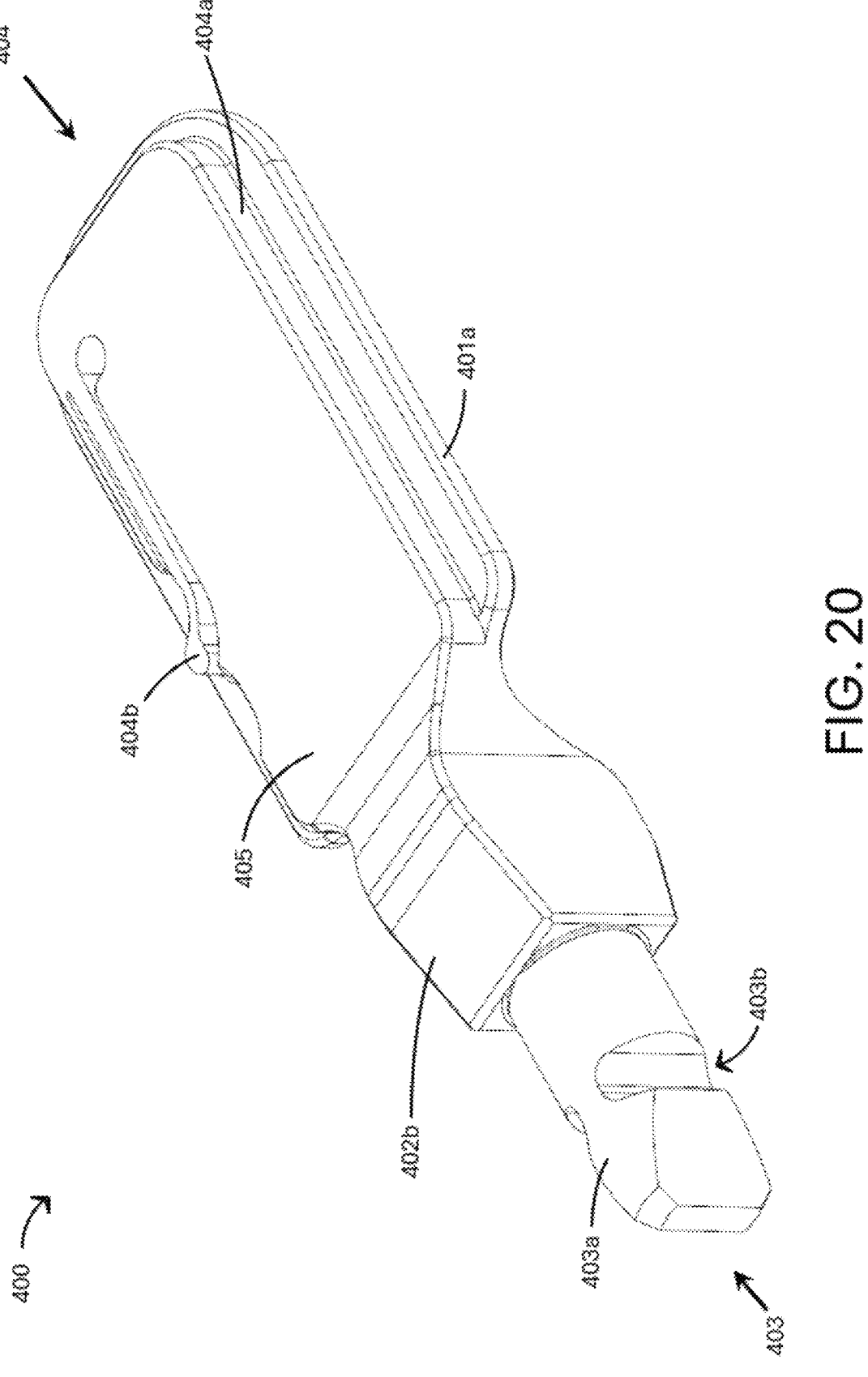
FIG. 20 shows a bottom perspective view of the exemplary detachable tool shown in FIG. 19.
Figures 21, 22:
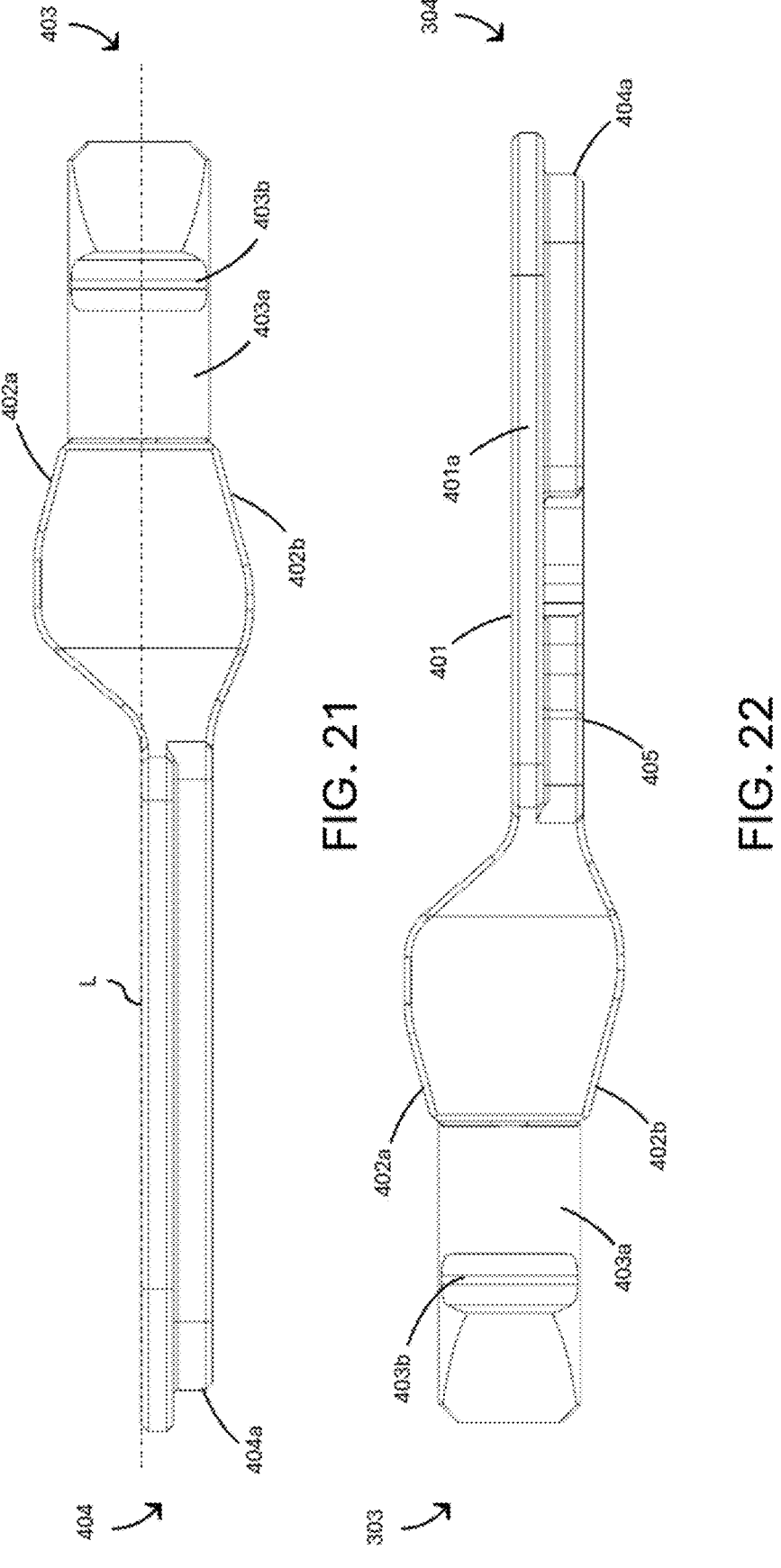
FIG. 21 shows a left side view of the exemplary detachable tool shown in FIG. 19.
FIG. 22 shows a right side view of the exemplary detachable tool shown in FIG. 19.
Figures 23, 24:
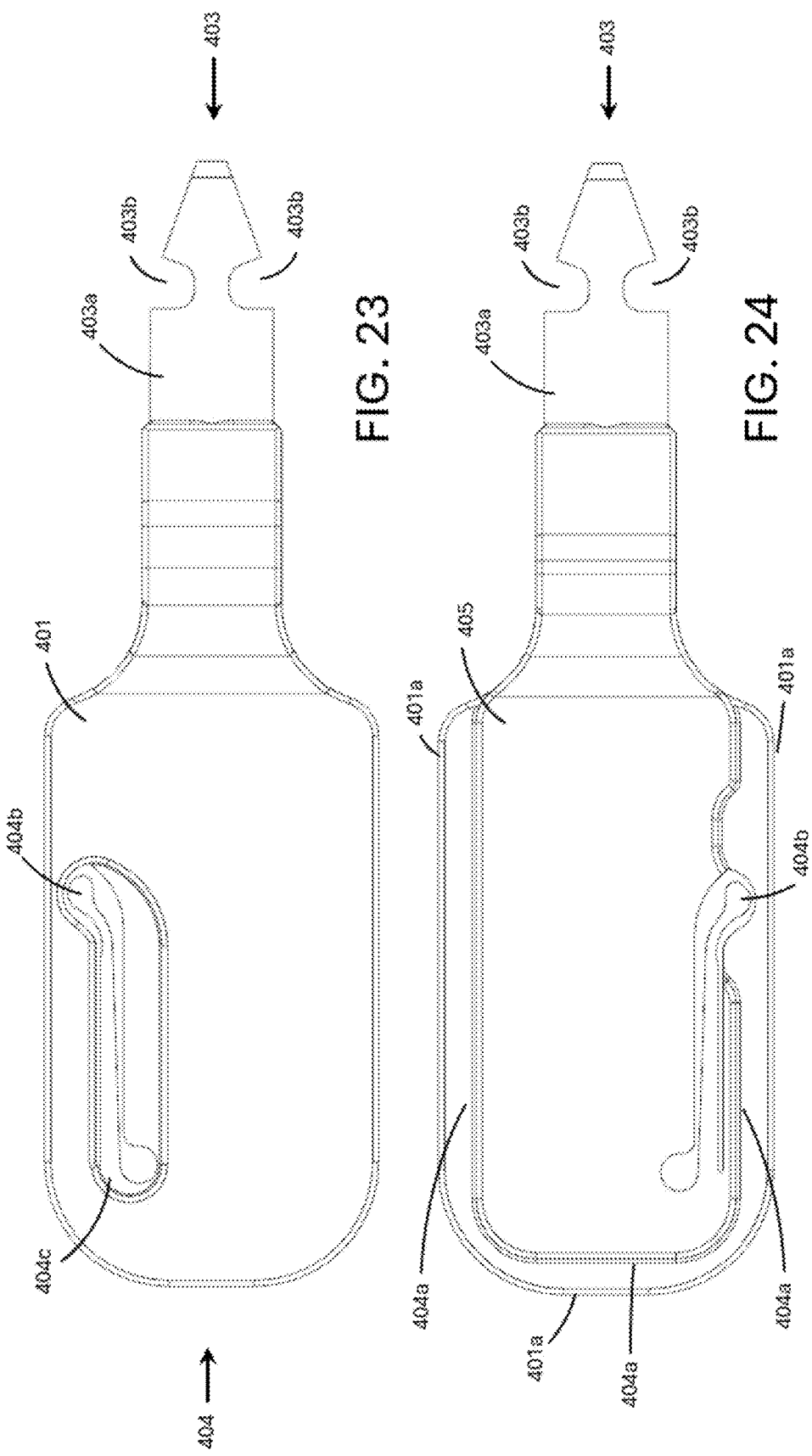
FIG. 23 shows a top view of the exemplary detachable tool shown in FIG. 19.
FIG. 24 shows a bottom view of the exemplary detachable tool shown in FIG. 19.
Figures 25, 26:
FIG. 25 shows a front view of the exemplary detachable tool shown in FIG. 19.
FIG. 26 shows a rear view of the exemplary detachable tool shown in FIG. 19.

FIG. 1 illustrates a perspective view of the disclosed distractor system 100 including a distractor device 200, a detachable tool 300 attached to the distractor device 200, a stemmed tibial implant 500 assembled to another detachable tool 400 (not imaged, see FIG. 2), wherein the other detachable tool 400 is also attached to the distractor device 200. The detachable tools can include, but are not limited to, a shape allowing for clearance with the stemmed tibial implant 500, or other instruments that require clearance with the detachable tool. Alternatively, the detachable tools can include but are not limited to cutting tools or generic surface preparation for subsequent implants or instruments. Additionally, the detachable tools may attach directly or indirectly to the distractor handle. For example, as detailed in FIGS. 11 and 19, the detachable tools may include a first end 303 and 403 that are male ends configured to detachably couple to the distractor first or second distracting member 203, 204 (FIG. 8) Alternatively, a separate collar, arm, connector, sleeve, fixators or the like may be used to couple the detachable tool to the collar, while coupling the collar to the distractor. It will be appreciated that the disclosed system and methods can be used with female components, external fixators to attach the detachable tools to the distractor. The use of modular, detachable tools as part of the distractor handle provides the ability to account for joint resection window space, final component sizes based on the resections/patient anatomy, it will be appreciated that the disclosed system and methods can be used with monolithic components and are within the scope of this disclosure. For example, in some embodiments, the detachable tools 300 and 400 are formed monolithically with the distractor device 200.

Figure 2:
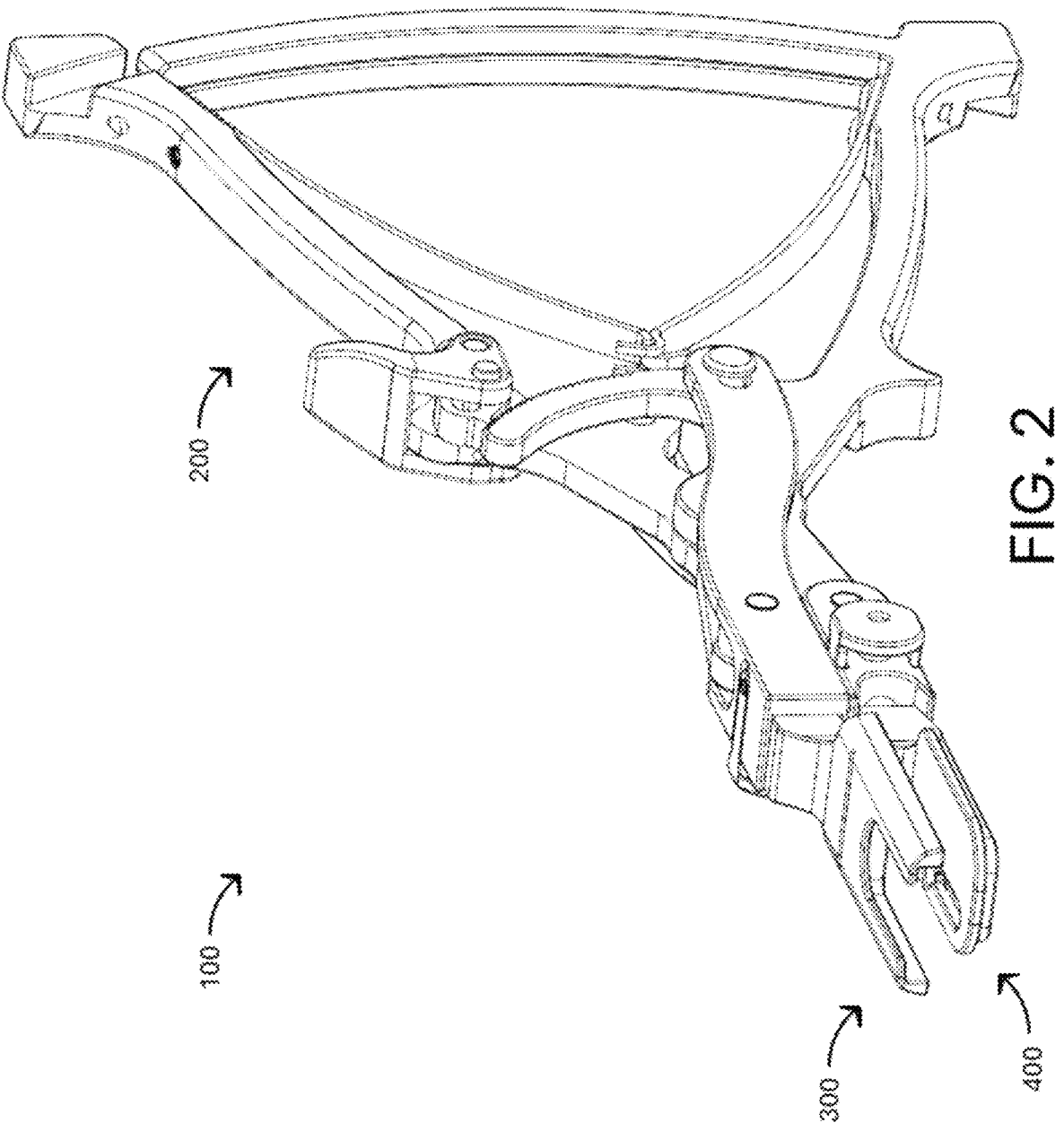
FIG. 2 illustrates an embodiment of a distractor system with detachable tools for joint space manipulation.

FIG. 2 illustrates a perspective view of a distractor system 100 including a distractor device 200, a detachable tool 300 attached to the distractor device 200, and another detachable tool 400 attached to the distractor handle. The detachable tool 400 can include but are not limited to paddle-like surfaces used for purposes but not limited to pressure distribution on a surface, compatibility with implants or other instruments. For example, as detailed in FIG. 19, the tool may be of paddle-like shape, where the bottom surface may be used distribute pressure on a bony surface, such that the top surface of a detachable tool 300 may contact an opposing bony surface. The distractor may then be utilized to increase the distance between the bony surfaces (to be referred to as 'the joint space') using the engageable arms 201 and 202. As shown in FIG. 1, a separate, but not limited to implant 500, may be coupled to the detachable tool 400. In other embodiments, other non-anatomic bodies may be coupled to the detachable tool.

Figure 6:
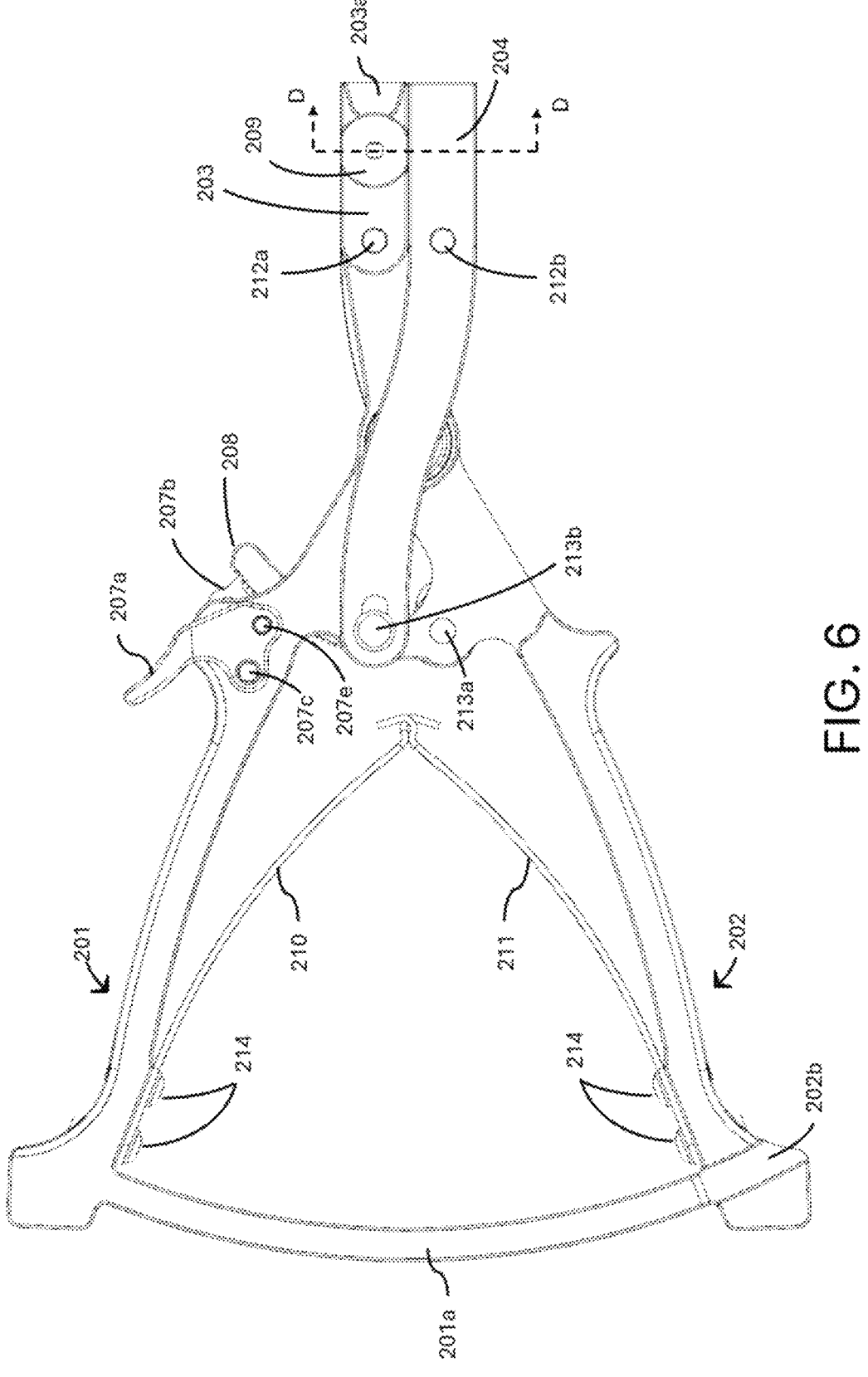
FIG. 6 shows a right side view of the distractor system shown in FIG. 3.
Figure 7:
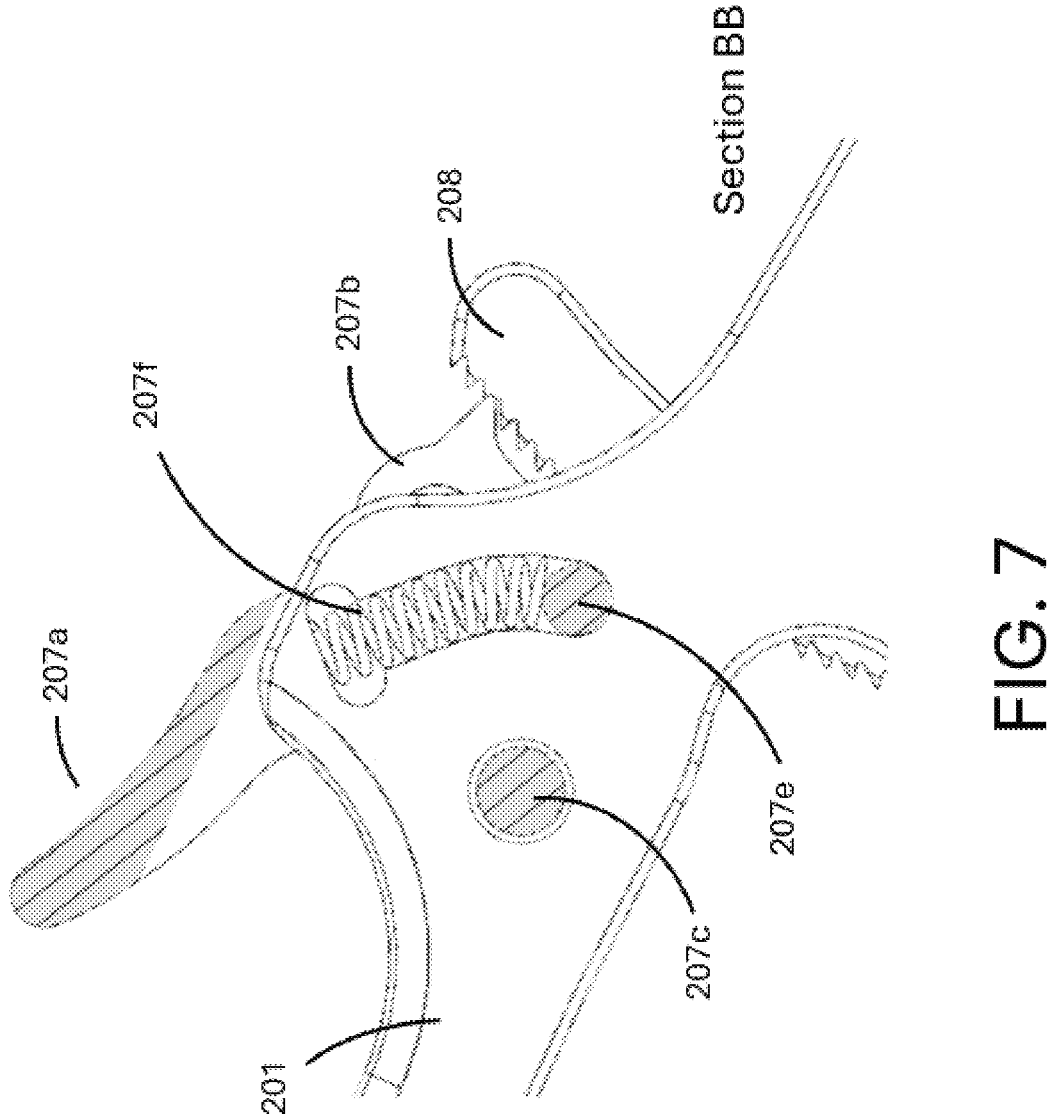
FIG. 7 shows a section view along section BB shown in FIG. 6.
Figure 8:
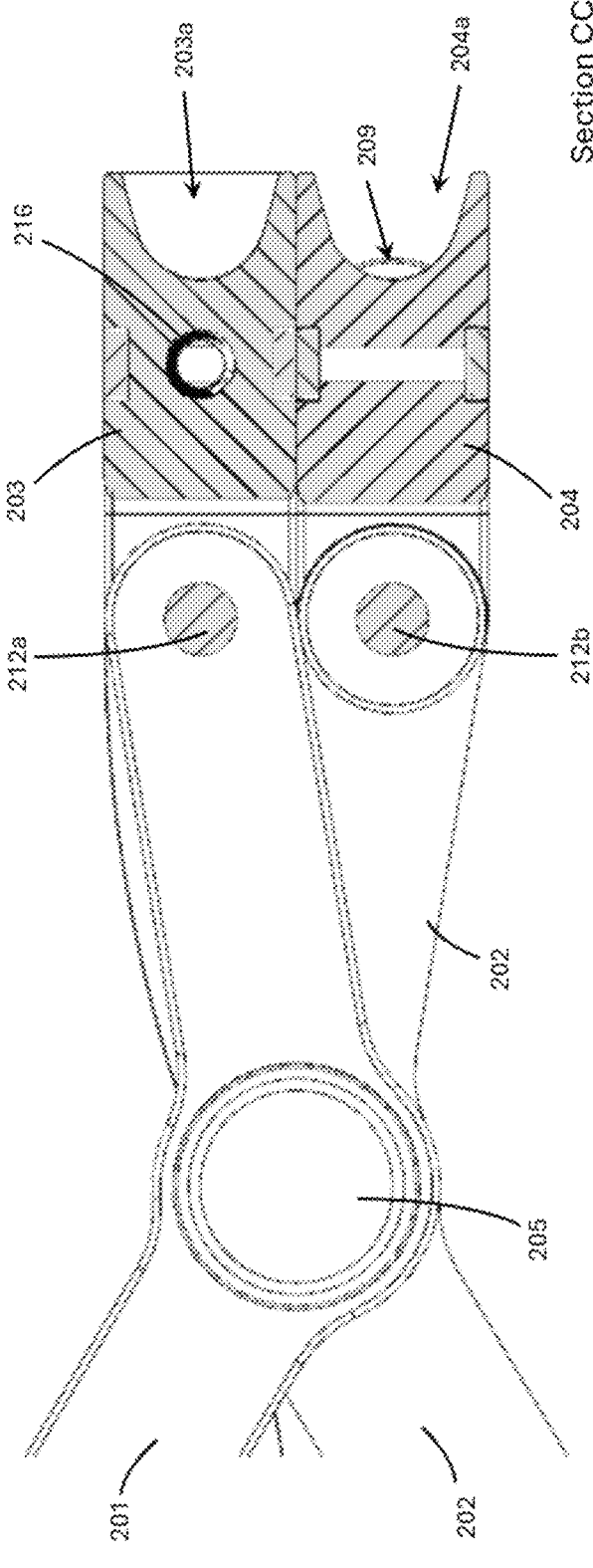
FIG. 8 shows a section view along section CC shown in FIG. 6.
Figure 9:
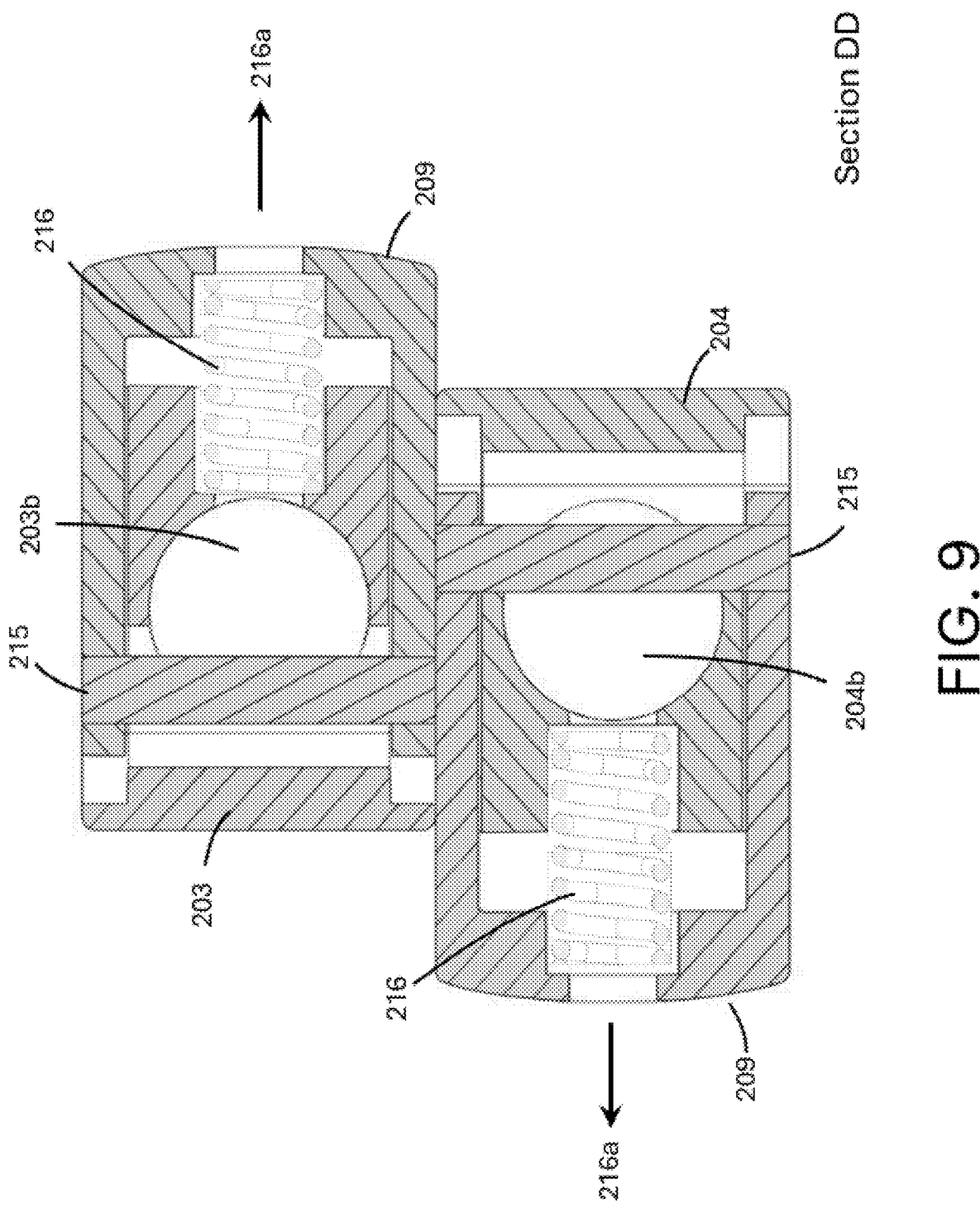
FIG. 9 shows a section view along section DD shown in FIG. 8.
Figure 10:
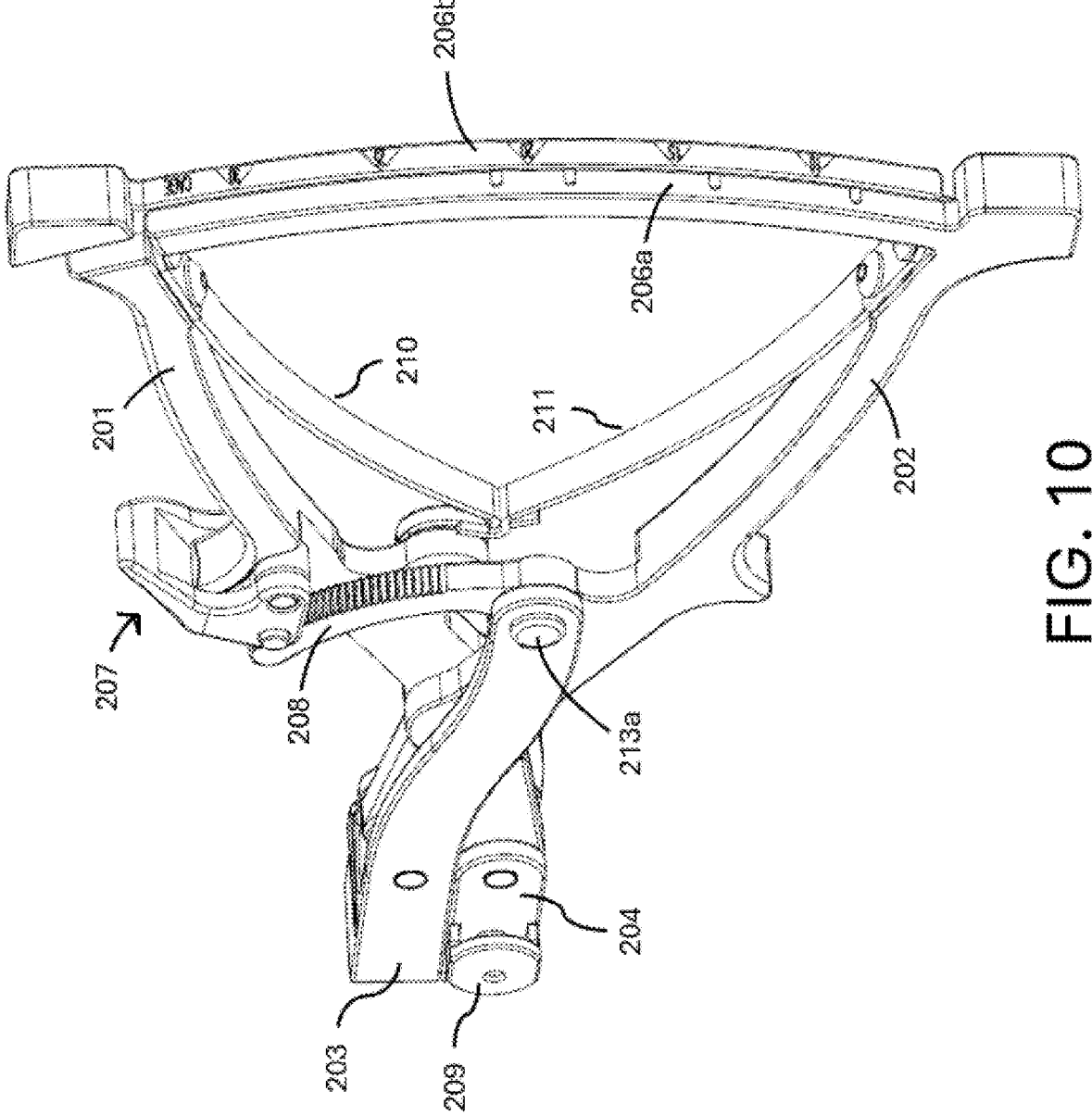
FIG. 10 shows a rear perspective view of the distractor system shown in FIG. 3.
Figure 32:
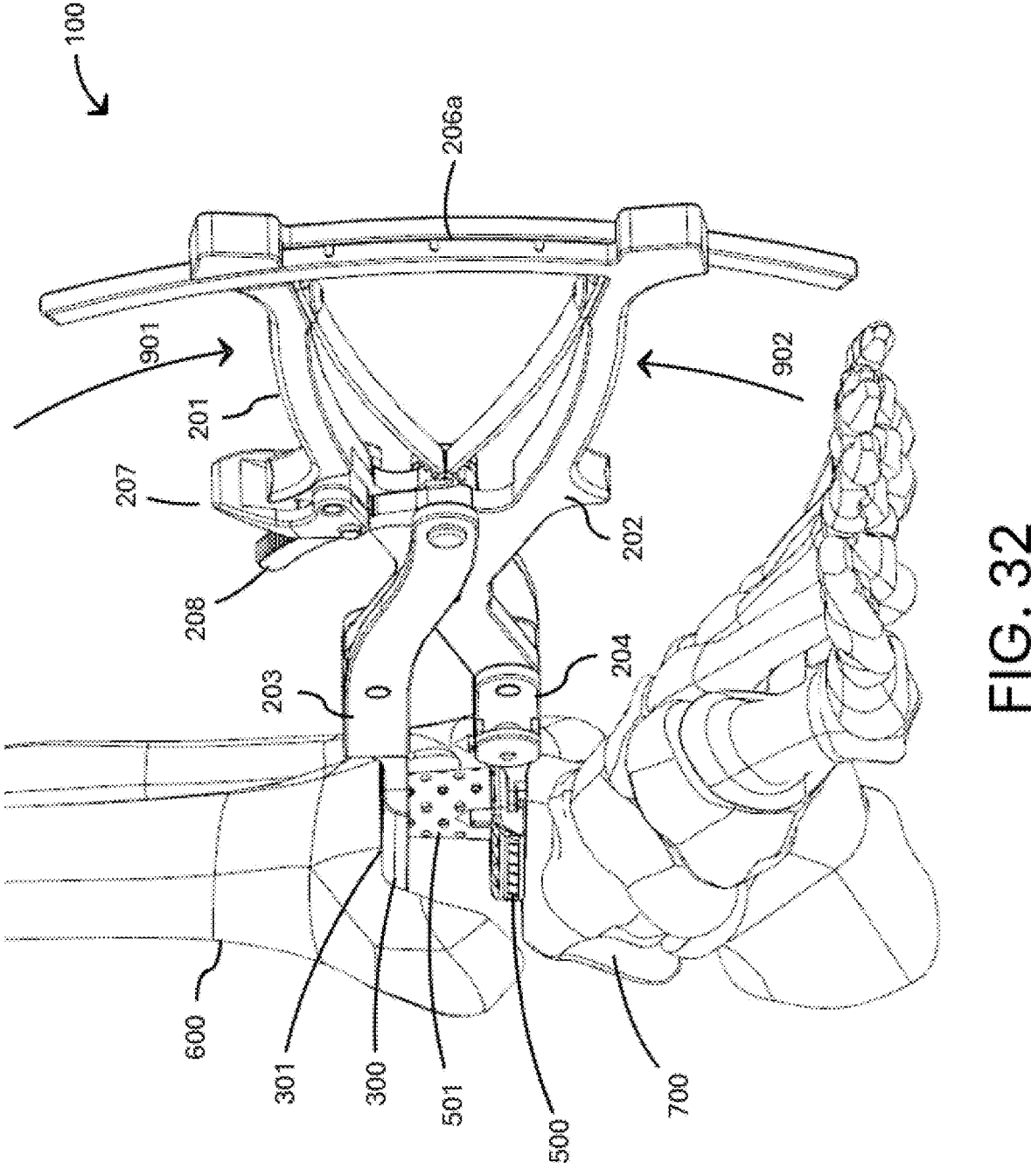
FIG. 32 shows a perspective view an exemplary subsequent insertion step following the step shown in FIG. 31.
Figure 33:
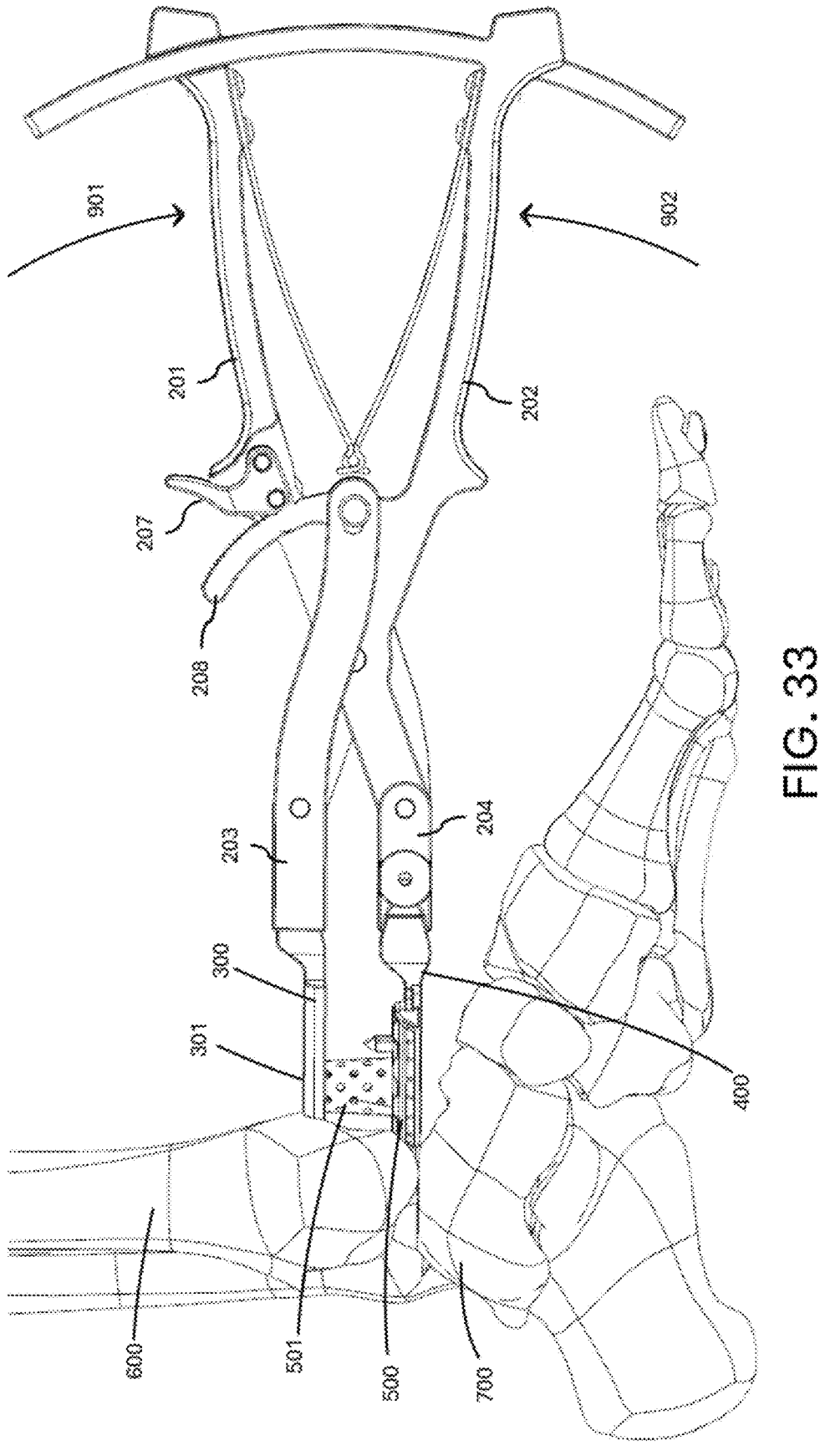
FIG. 33 shows a left side view of the exemplary subsequent insertion step shown in FIG. 32.

FIGS. 3-10 illustrate various views of the distractor device 200 according to some embodiments. The disclosed distractor is composed of two user engageable arms 201 and 202. As shown in FIGS. 8, 201 and 202 are pivotably engaged by an axle pin 205. According to some embodiments, the engageable arms may additionally include a transverse arm 201a and 202a for each respective engageable arm. As shown in FIG. 10, the transverse arm includes indicators 206a and 206b. As shown in FIGS. 32-33, the indicators 206a and 206b may be used to evaluate the distance between the detachable tools 300 and 400.

The disclosed distractor is additionally composed of a first and second distracting member 203 and 204. With respect to FIGS. 4 and 6, the first end of the first distracting member 203 beginning at the pivot pin 213a, and the second end of the first distracting member being the opening defined by 203a as shown in FIG. 6. The first distracting member is pivotably connected to the second engageable arm 202 via the pivot pin 213a and is also pivotably connected to the first engageable arm 201 via the pivot pin 212a.

Figure 4:
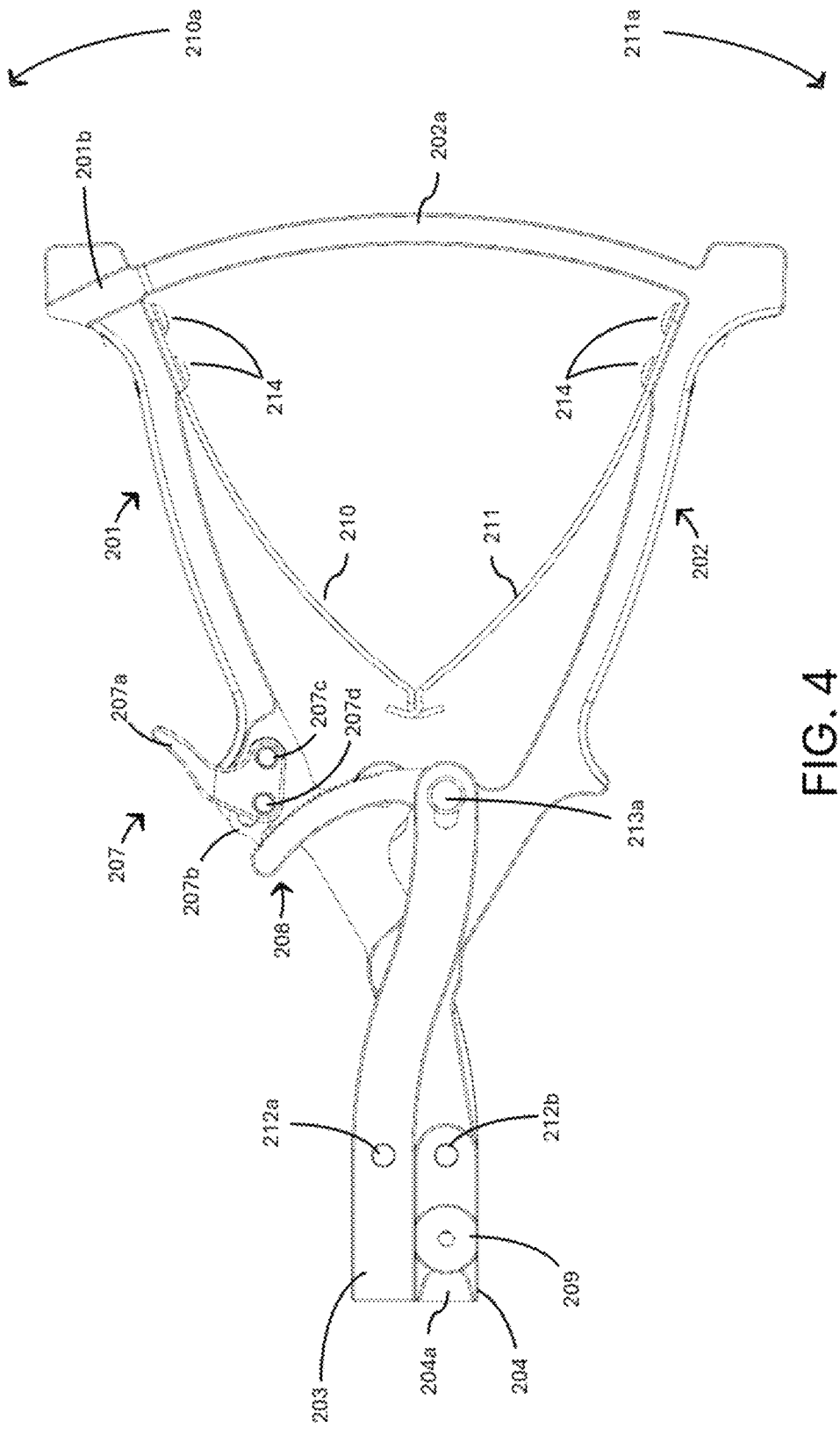
FIG. 4 is a left side view of the distractor system shown in FIG. 3.

Conversely, the first end of second distracting member 204 beginning at the pivot pin 213b, and the second end of the second distracting member being the opening defined by 204a as shown in FIG. 4. The second distracting member is pivotably connected to the first engageable arm 201 via the pivot pin 213b and is also pivotably connected to the second engageable arm 202 via the pivot pin 212b.

The disclosed distractor additionally contains two leaf springs 210 and 211 that are configured to apply a distracting force between the engageable arms 201 and 202. In other embodiments, other mechanical mechanisms, including, but not limited to, coil springs are used to apply this distracting force. As shown in FIGS. 4 and 6, the leaf-springs are fixated to the engageable arms 201 and 202 using threaded bolts 214 but may be fixated to the arms via similar methods such as rivets and weld junctions.

Figure 5:
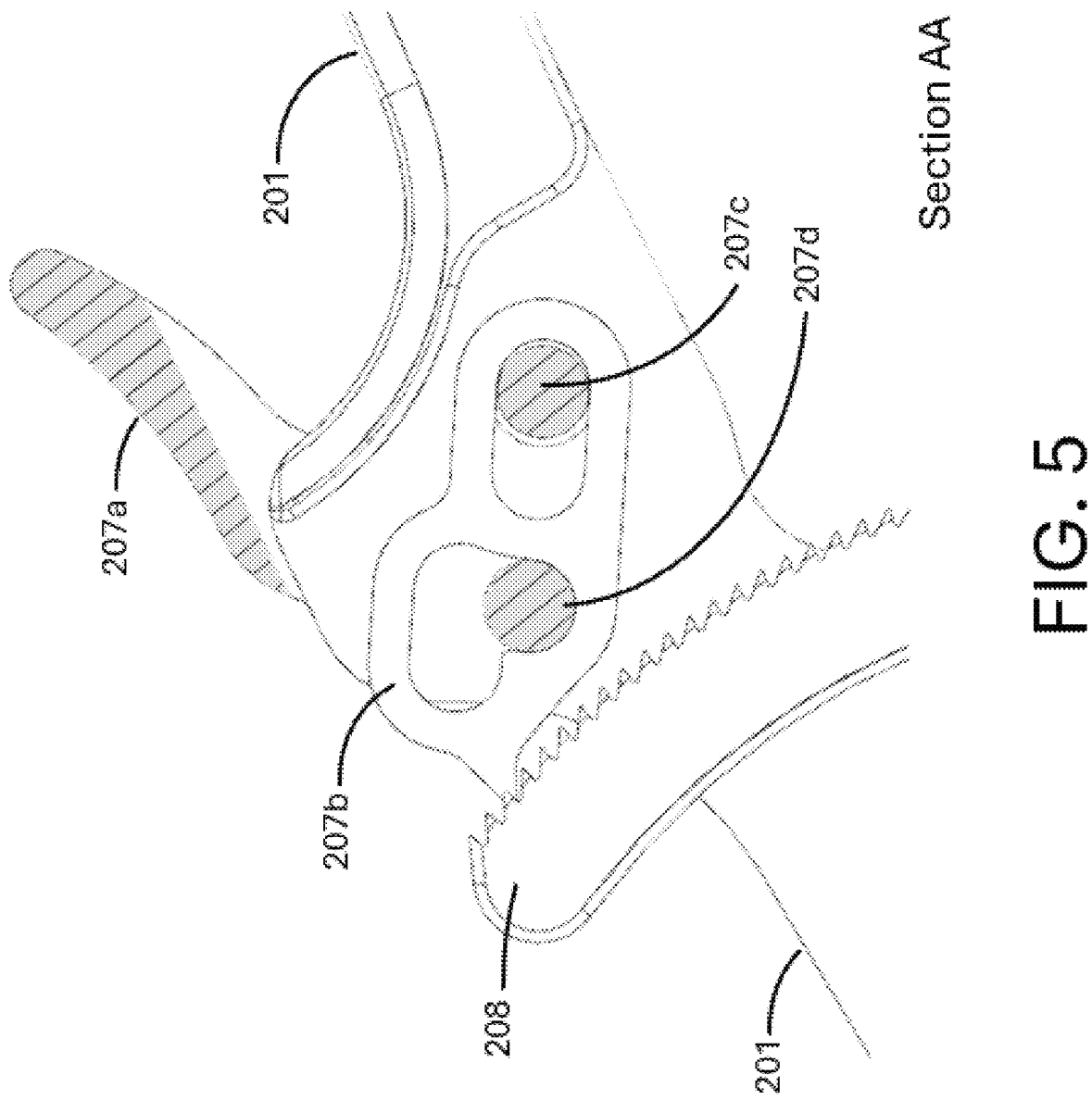
FIG. 5 shows a section view along section AA shown in FIG. 4.

In some embodiments, the distractor device 200 includes a locking mechanism 207 and teeth 208. As more easily shown in FIG. 10, the teeth 208 are connected to a transverse arm attached to the second engageable arm 202. The locking mechanism 207 includes a latch 207a that is toggled by the user, a pawl 207b that engages the teeth 208, a main pivot pin 207c, secondary pivot pins 207d and 207e, and a coil spring 207f. FIGS. 5 and 7 are Section Views AA and BB of FIG. 3. During use, the pawl 207b will engage the teeth 208, acting as a provisional lock while the leaf-springs are applying forces 210a and 211a. During use, the distance between 203a and 204a will increase as shown in FIGS. 32-33 (referred to as an 'open' or 'distracted' state). During use, the transverse arm 201a of the first engageable arm 201 will cross through a groove 202b in the second engageable arm 202 (FIG. 6). Conversely, the transverse arm 202a of the second engageable arm 202 will cross through a groove 201b of the first engageable arm (FIG. 4). Upon toggle by the user, the pawl 207b will disengage the teeth 208, thereby allowing forces 210a and 211a to return the spreader to its 'closed' or 'non-distracted' state. However, it will be appreciated that the locking mechanism may include a singular component or feature such as an external pin that crosses between the engageable arms 201 and 202, or simplified ratchet-and-pawl constructs.

Figure 3:
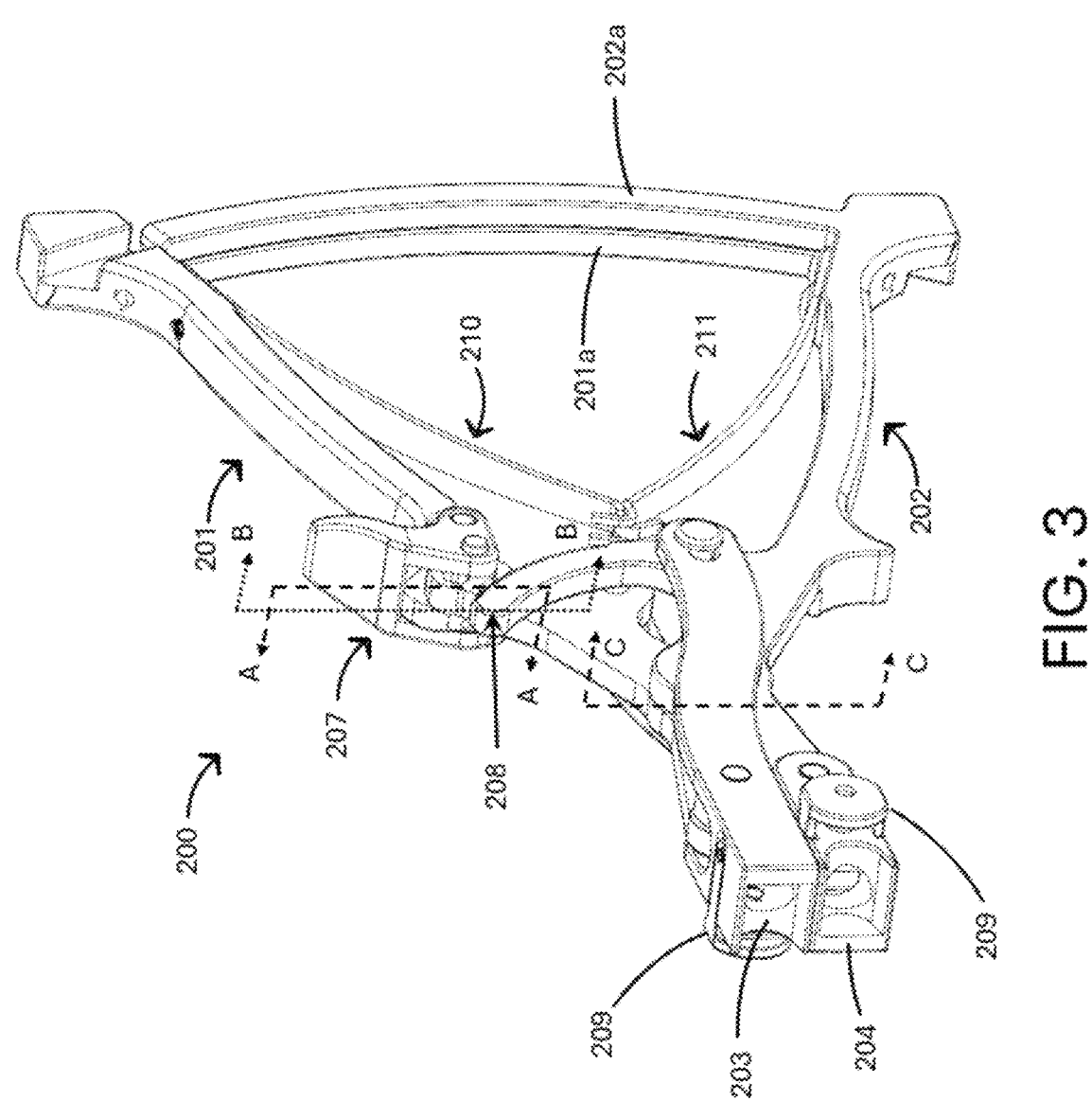
FIG. 3 shows a perspective view of the distractor system shown in FIG. 1 without detachable tools.

FIG. 8 is a Section View CC of FIG. 3 to more easily illustrate the pivot points of the user engageable arms 201 and 202, and first and second distracting members 203 and 204.

The disclosed distractor additionally includes a coupling mechanism to detachably couple the detachable tools 300 and 400. As shown in FIGS. 3, 8, and 9, the first and second distracting members each include a button 209. With respect to FIG. 9 (Section View DD of FIG. 6), the button 209 is attached to the distracting members 203 and 204 using crossing pins 215. The coupling mechanism additionally includes springs 216 that apply a spring force on the button 209, as shown by forces 216*a*. The crossing pins 215 engage the respective pockets 303*b* and 403*b* in the detachable tools 300 and 400, respectively, to prevent unintentional disassembly of the detachable tools to the distractor. Additionally, the first and second distracting members include a female pocket 203*b* and 204*b* to accept a male first end 303 and 403. However, it will be appreciated that the female pocket may include non-cylindrical shapes. Additionally, as previously stated, it will be appreciated that the connecting features encompass alternative male connections in place of female connections, or external fixation methods.

FIG. 10 is a rear-perspective view of the distractor device 200. According to some embodiments, the indicators 206*a* and 206*b* on transverse arms 201*a* and 202*a* may be used to evaluate the space between the detachable tools 300 and 400. In this embodiment, the markings provide preliminary indications concerning implant sizes that are compatible with the joint space. It will be appreciated that the markings on at least one of the transverse arms, or combination of markings on the at least one transverse arms may include engravings, embossings, laser marking, material etching, or other methods of marking/delineation.

Figure 34:
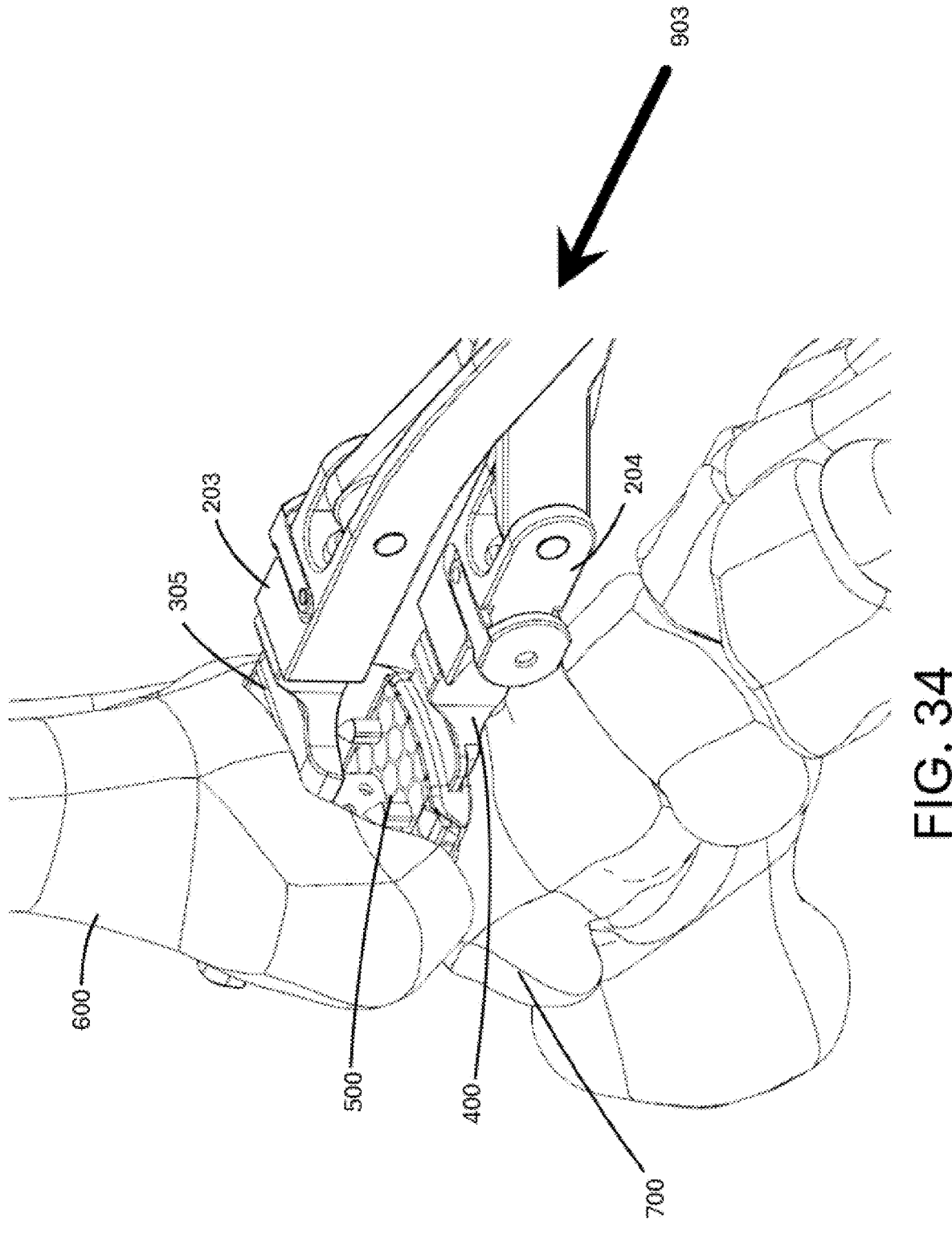
FIG. 34 shows a perspective view an exemplary subsequent insertion step following the step shown in FIG. 32.
Figure 35:
FIG. 35 shows a left side view of the exemplary subsequent insertion step shown in FIG. 34.

FIGS. 11-18 illustrate various views of a detachable tool 300 according to some embodiments. The disclosed detachable tool 300 is composed of a first end 303 and a second end 304, which define a length L. In this embodiment, the first end 303 includes a male connecting body to connect to either the first or second distracting members 203 and 204. In this embodiment, the male connecting body includes a cylindrical-like body 303*a* and a female pocket 303*b*. In this embodiment, the cylindrical body 303*a* is configured to have clearance with either pocket 203*b* or 204*b*. As more easily shown in FIGS. 13 and 14, the surfaces 302*a* and 302*b* are configured to interface with the female pockets 203*a* and 204*a* of the distracting members 203 and 204 of the distractor (FIG. 8). In this embodiment, the first end 303 additionally includes a biasing member 306 to allow engagement of the cylindrical body 303*a*, female pocket 303*b*, and surfaces 302*a* and 302*b*, with the female pocket 203*b*, crossing pin 215, and pocket 203*a* respectively. With respect to FIG. 9 and FIG. 11, the biasing member 306 allows the detachable tool 300 to engage the first distracting member 203 such that face 301 is facing up, wherein 301 is intended to interface with at least one of two opposing bony surfaces. However, the biasing member 306 will prevent assembly of the detachable tool 300 to the first distracting member 203 such that the face 301 is facing down. Similarly, in this embodiment, the detachable tool may alternatively be attached to distracting member 204. In this orientation, the biasing member 306 allows the detachable tool 300 to engage the second distracting member 204 such that face 301 is facing down. However, it will be appreciated that the disclosed detachable tools may or may not include biasing members for assembly. In this embodiment, the detachable tool 300 includes a channel 305 that may be used as a depth indicator during the insertion step (FIG. 34). However, it will be appreciated that the disclosed detachable tools may or may not include a female indicator, male indicator, laser markings, or the like.

Figure 31:
FIG. 31 shows a perspective view of an exemplary initial insertion step of use of the exemplary distractor system shown in FIG. 1.
Figure 37:
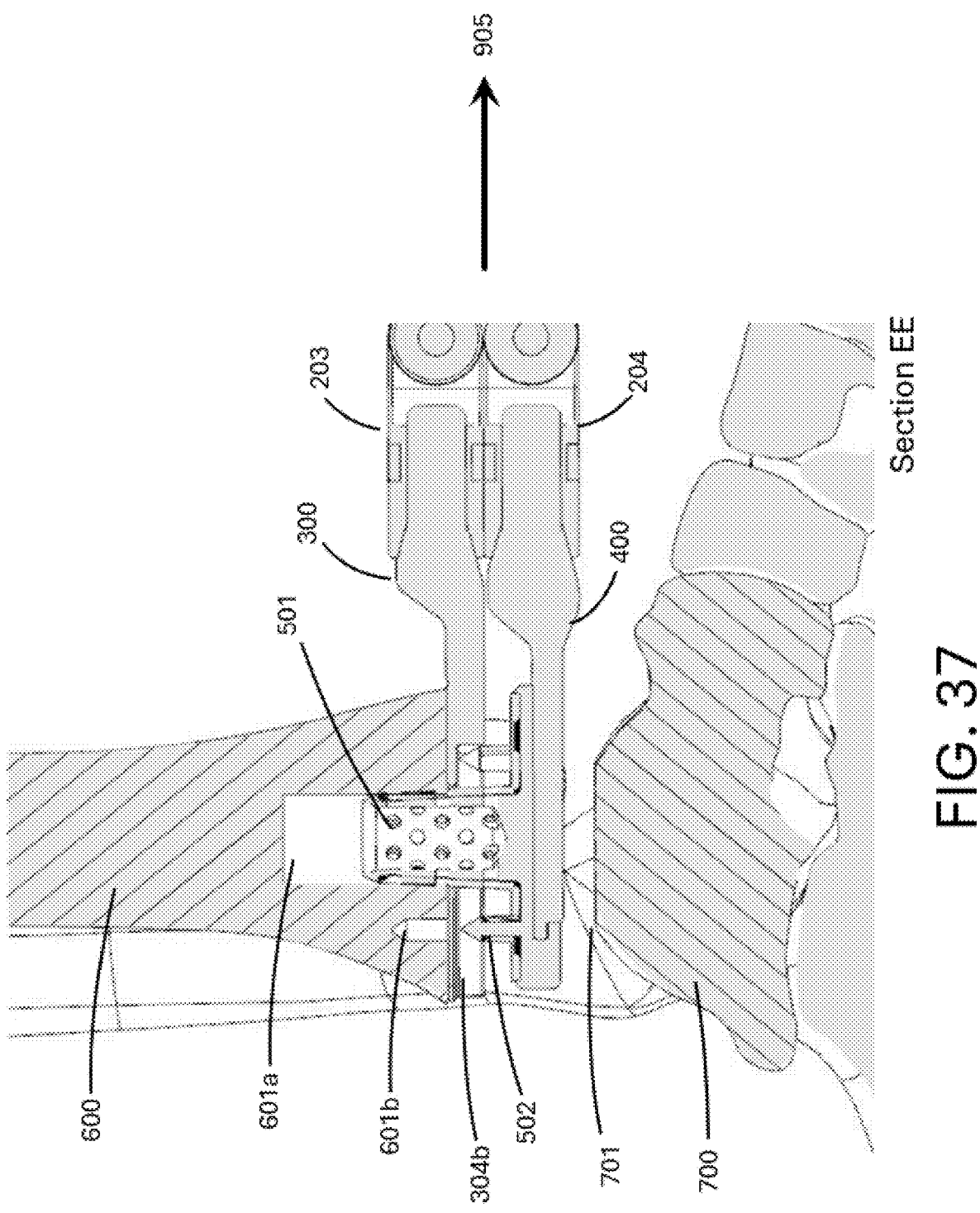
FIG. 37 shows a section view along section EE shown in FIG. 36.

As shown more easily in FIGS. 11, 12, 15, 16, and 17, in this embodiment, the second end 304 may include at least one pocket 304*a* that allows for clearance of the conical cage 501 of the implant 500 (FIGS. 1, 31, and 37). In this embodiment, the second end 304 may include a second pocket 304*b* that allows for clearance of the peripheral fixation pegs 502 of the implant 500 (FIG. 37). According to some embodiments, the conical cage 501 and the peripheral fixation pegs 502 are fixation features of a stemmed tibial implant 500. However, while this embodiment includes pockets 304*a* and 304*b* configured to have clearance with the conical cage 501 and the peripheral fixation pegs 502, it will be appreciated that the detachable tools may include bodies that do not have pockets, or any number of pockets. As noted above, while the exemplary embodiments discussed herein show the distractor system 100 used in conjunction with an exemplary stemmed tibial implant, in other embodiments, the distractor device may be used in conjunction with (e.g., the detachable tool 400 may releasably engage) another non-anatomic body, such as a non-stemmed implant, an instrument body, or the like.

FIGS. 19-26 illustrate various views of a detachable tool 400 according to some embodiments. The disclosed detachable tool 400 is composed of a first end 403 and a second end 404, which define a length L. In this embodiment, the first end 403 includes a male connecting body to connect to either the first or second distracting members 203 and 204. In this embodiment, the male connecting body includes a cylindrical-like body 403*a* and a female pockets 403*b*. In this embodiment, the cylindrical body 403*a* is configured to have clearance with either pocket 203*b* or 204*b*. As more easily shown in FIGS. 21 and 22, the surfaces 402*a* and 402*b* are configured to interface with the female pockets 203*a* and 204*a* of the distracting members 203 and 204 of the distractor (FIG. 8). With respect to FIG. 9 and FIG. 19, the two pockets 403*b* allow the detachable tool 400 to engage the first distracting member 203 such that face 401 is either facing up or down. Similarly, in this embodiment, the detachable tool may alternatively be attached to distracting member 204. The two pockets 403*b* allow the detachable tool 400 to engage the second distracting member 204 such that face 401 is either facing up or down.

In this embodiment, second end 404 is configured to interface with the stemmed tibial implant 500. As shown more easily in FIGS. 20 and 24, end 404 includes an upper shelf 401*a*, lower shelf 404*a*, and at least one feature 404*b*, and may include a pocket 404*c*, wherein pocket 404*c* may be used to aid in manufacturing of feature 404*b*. According to some embodiments, the feature 404*b* may include a flexure to prevent unintended disassembly of the detachable tool 400 from the stemmed tibial implant 500. However, it will be appreciated that feature 404*b* may include a sliding pin mechanism, leaf-spring, external pin, or other methods of interfacing with the detachable tool 400 with the stemmed tibial implant 500 to prevent disassembly. Similarly, it will be appreciated that the at least one feature 404*b* may include several features in any amount, on any face along 404*a* or 401. According to some embodiments, 404*a* may include a shelf-like cutout or protrusion to interface with the stemmed tibial implant 500. As discussed above, the detachable tool 400 is described herein with specific reference to engagement with the implant 500, but in other embodiments, the detachable tool 400 may be configured to releasably engage another non-anatomic body, such as a non-stemmed implant, an instrument body, or the like.

Figures 27, 28:
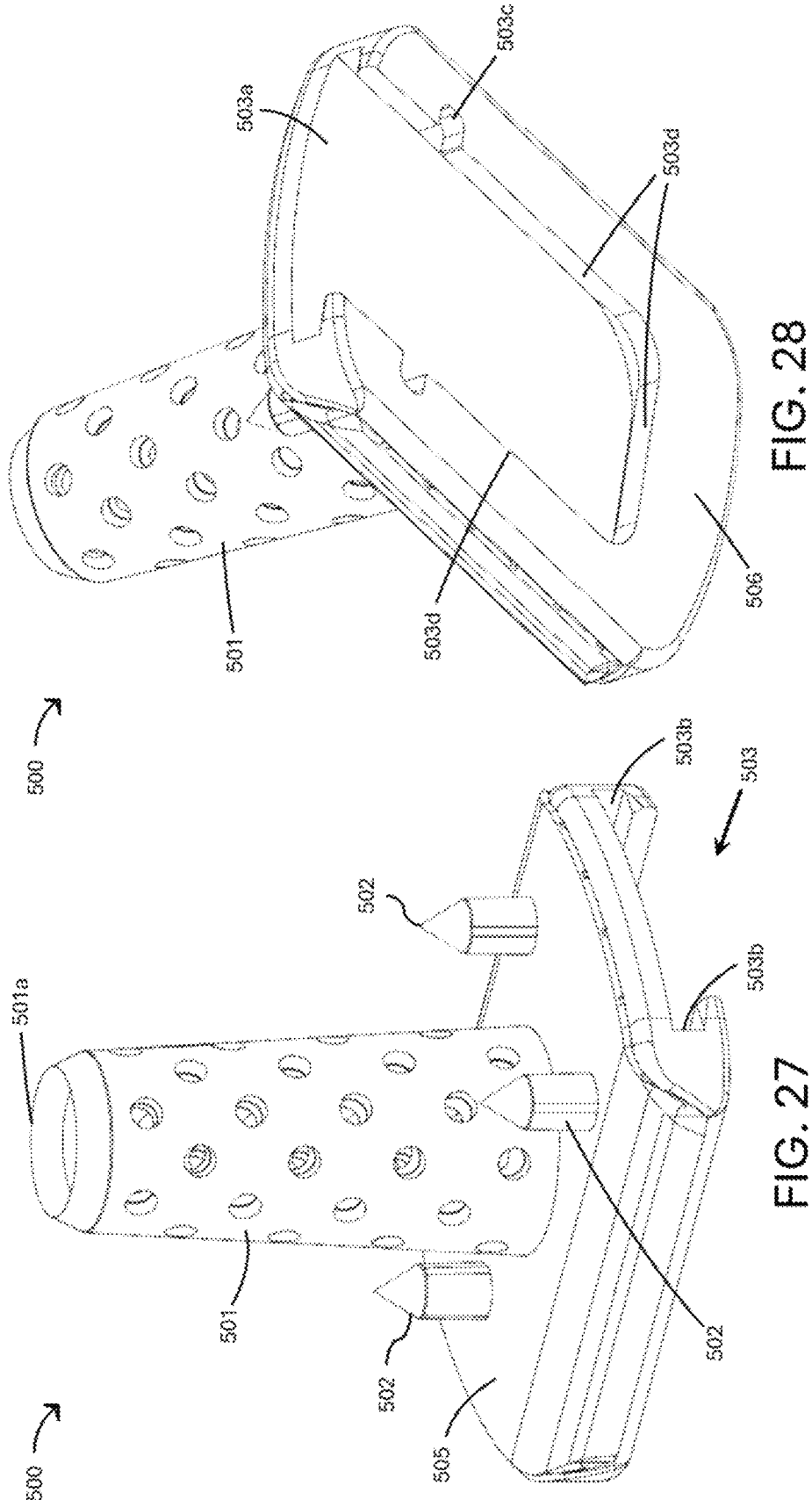
FIG. 27 shows a perspective view of an exemplary stemmed tibial implant.
FIG. 28 shows a bottom perspective view of the exemplary stemmed tibial implant shown in FIG. 27.

FIG. 27 and FIG. 28 illustrate two views of the stemmed tibial implant 500 according to some embodiments. In this embodiment, the stemmed tibial implant 500 includes primary fixation features, e.g., a centrally located conical cage 501 and peripheral fixation pegs 502. In this embodiment, the conical central cage 501 may be configured to be inserted into a prepared intramedullary canal 601a. Central cage 501 may additionally include an opening at the top 501a of the conical cage 501. In this embodiment, the peripheral fixation pegs 502 may be configured to be inserted into prepared broached peripheral holes 601b. It will be appreciated that, in other embodiments, the stemmed tibial implant 500 includes fixation features other than the conical cage 501 and the peripheral fixation pegs 502, which may include non-conical shapes such as a cylinder, a prism, or other geometric shapes in various widths, lengths, and quantity.

The stemmed tibial implant 500, according to some embodiments, may include an opening 503 that may be configured to detachably couple to a detachable tool 400. The opening 503 includes a superior surface 503a, upper inner surfaces 503b, at least one notch 503c (e.g., a notch, pocket, indent, or the like), and lower inner surfaces 503d.

The stemmed tibial implant 500, according to some embodiments, may include a bone contacting surface 505 and a surface 506 that may or may not contact bone.

As shown more easily in FIGS. 23, 24, 27 and 28, according to some embodiments, face 401 of the detachable tool 400 is configured to interface with surface 503a of the opening 503 of the stemmed tibial implant 500, upper shelf 401a is configured to interface with upper inner surfaces 503b, feature 404b is configured to interface with notch 503c, lower shelf 404a is configured to interface with lower surfaces 503d.

Figure 30:
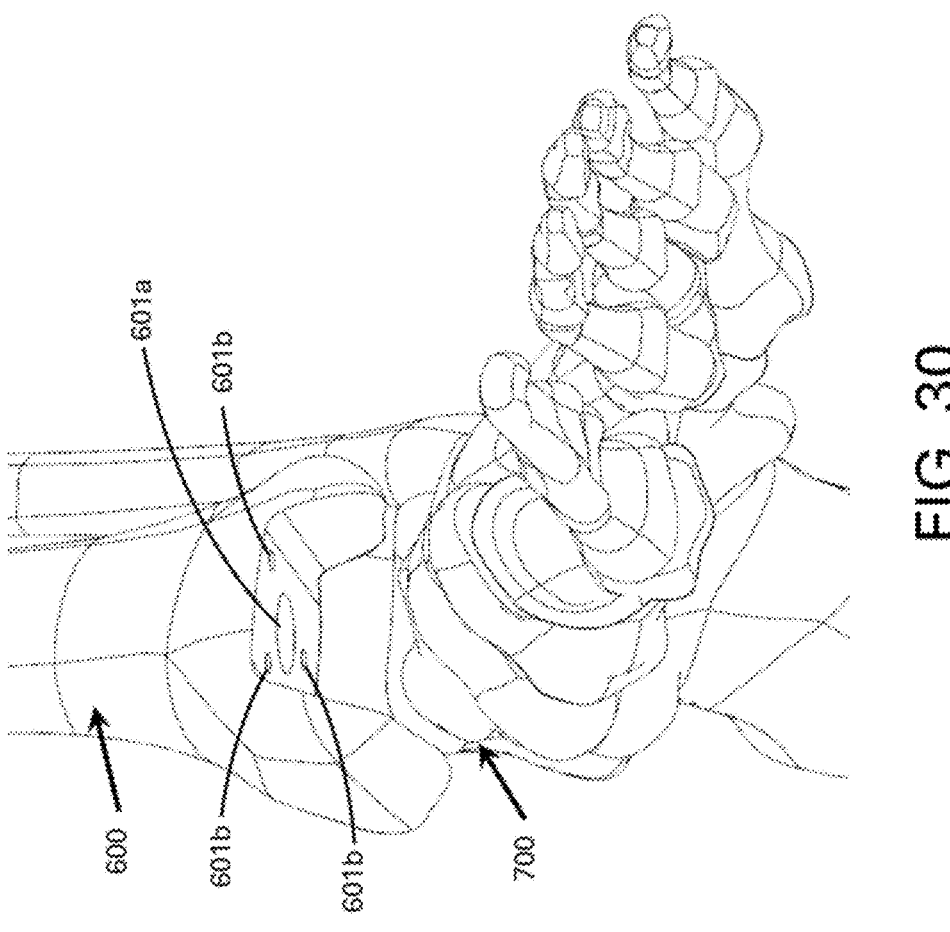
FIG. 30 shows a perspective view of the prepared ankle joint shown in FIG. 29.
Figure 29:
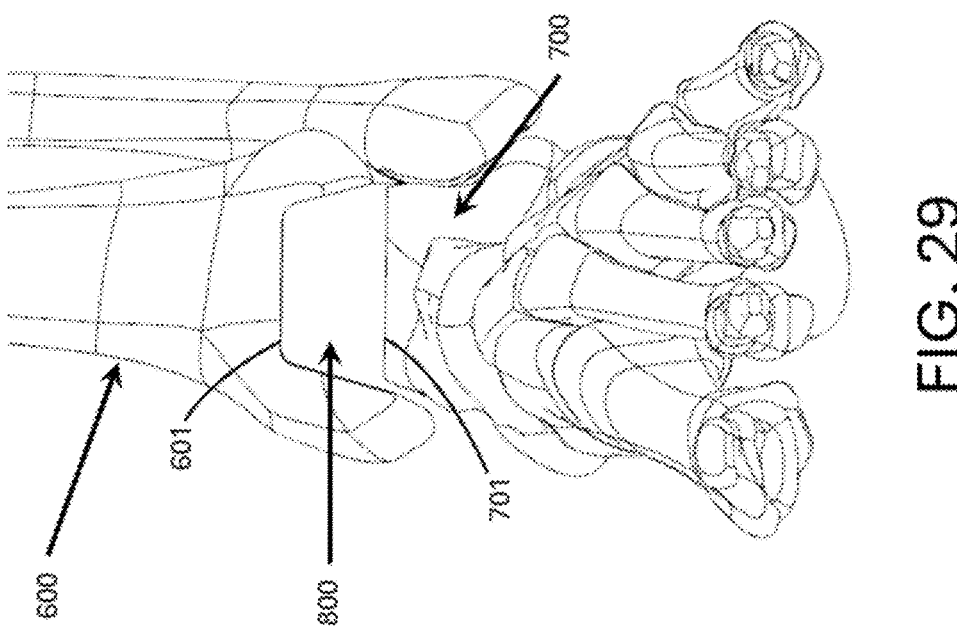
FIG. 29 shows an anterior view of a prepared ankle joint prior to use of an exemplary distractor system.

FIG. 29 and FIG. 30 illustrate a prepared tibia 600 and talus 700 for a total ankle replacement, with a joint space 800 comprising the space between resected bony surfaces 601 and 701. In some embodiments, the prepared tibia includes a prepared intramedullary canal 601a, and peripheral holes 601b. It will be appreciated that joint space 800 may include zero, one, or two prepared bony surfaces.

FIGS. 31-44 illustrate the steps of distracting the prepared tibia 600 and talus 700 with the disclosed distractor system 100 inserting a stemmed tibial implant 500 according to some exemplary embodiments. In other embodiments, the distractor system may be adapted for use in another joint that includes two opposing bony ends such as the knee, hip, or the like. Additionally, it will be appreciated that the disclosed system may include the stemmed tibial implant 500 to be inserted into either prepared bone (e.g., the tibia 600 or the talus 700). In other embodiments, the exemplary distractor system 100 may be used in conjunction with an instrument trial, a non-stemmed implant, a subsequent preparation tool, or the like in substantially the same manner as described herein with reference to the exemplary stemmed tibial implant 500.

According to some embodiments, the first step includes assembling the distractor system 100 as shown in FIG. 2 and subsequently assembling the implant 500 as shown in FIG. 1. The distractor system 100 is then introduced into the joint space 800 as shown in FIG. 31. In this embodiment, face 301 is oriented such that it may be flush with the prepared surface 601. Additionally, with respect to FIG. 31, the top 501a of the implant 500 may be more proximal than face 301, wherein the cage 501 will prevent further insertion into the joint space 800.

With respect to FIGS. 32 and 33, in this embodiment, the user applies forces 901 and 902 to the engageable arms 201 and 202, wherein the space between the detachable tools 300 and 400 increases. Upon application of forces 901 and 902, face 301 is more proximal than the top 501a of the implant 500 (not seen). However, in this embodiment, even after the application of forces 901 and 902 the top 501a of the implant 500 may still be more proximal than face 301. In this embodiment, the indicators 206a may be used to evaluate the joint space or provide instructions for additional bony resections. In this embodiment, as forces 901 and 902 are applied, the locking mechanism 207 and teeth 208 prevent the distractor device 200 from returning to its original, 'closed' state.

In this embodiment, the user applies force 903 to further insert the distractor system into joint space 800 as shown in FIG. 34. In this embodiment, channel 305 of the detachable tool 300 may be used to indicate that the conical cage 501 is aligned to the prepared intramedullary canal 601a.

Figure 36:
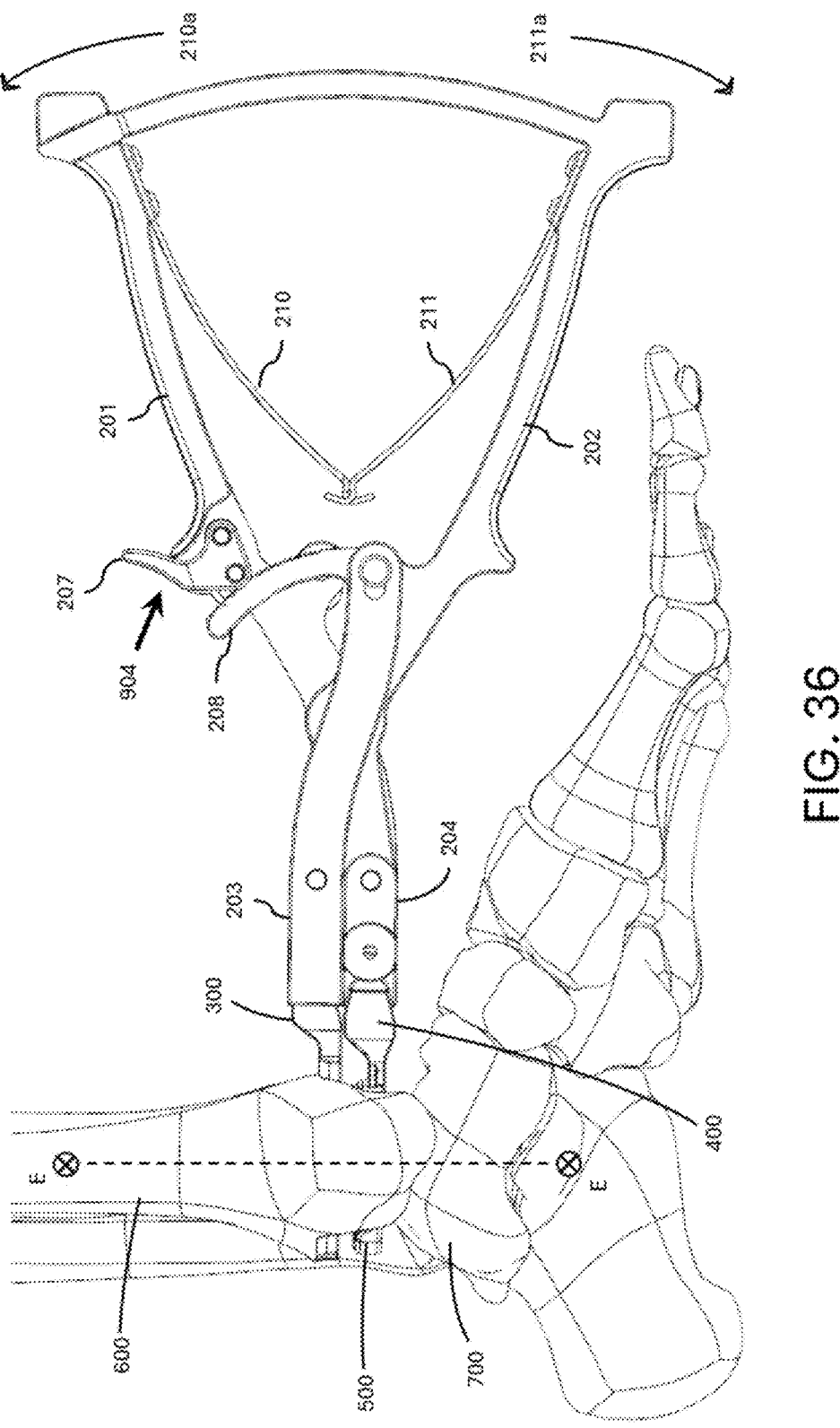
FIG. 36 shows a left side view of an exemplary subsequent insertion step following the step shown in FIG. 35.

With respect to FIG. 36, in this embodiment, the user applies force 904 to release the locking mechanism 207 from the teeth 208, wherein the leaf springs 210 and 211 apply forces 210a and 211a to return the distractor device 200 to a 'closed' state. With respect to FIG. 37, Section View EE of FIG. 36, in this embodiment, the distractor system 100 'closed' such that the conical cage 501 is within the prepared intramedullary canal 601a.

Figure 38:
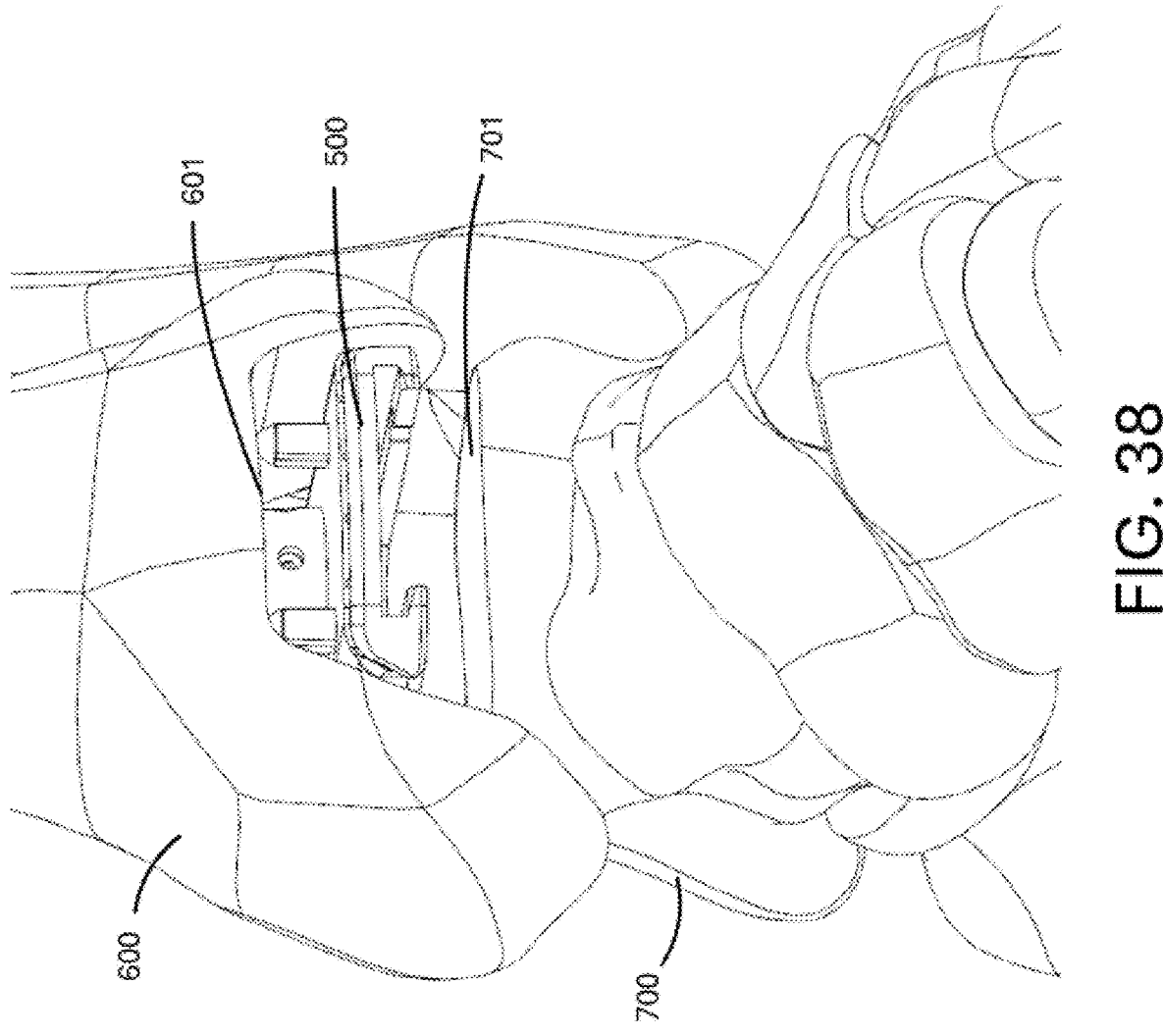
FIG. 38 shows a section view of an exemplary stemmed tibial implant as positioned in the ankle joint following the step shown in FIG. 36.

In this embodiment, the user removes the distractor device 200 using force 905, wherein the implant remains in the joint space (FIG. 38).

Figures 39, 40:
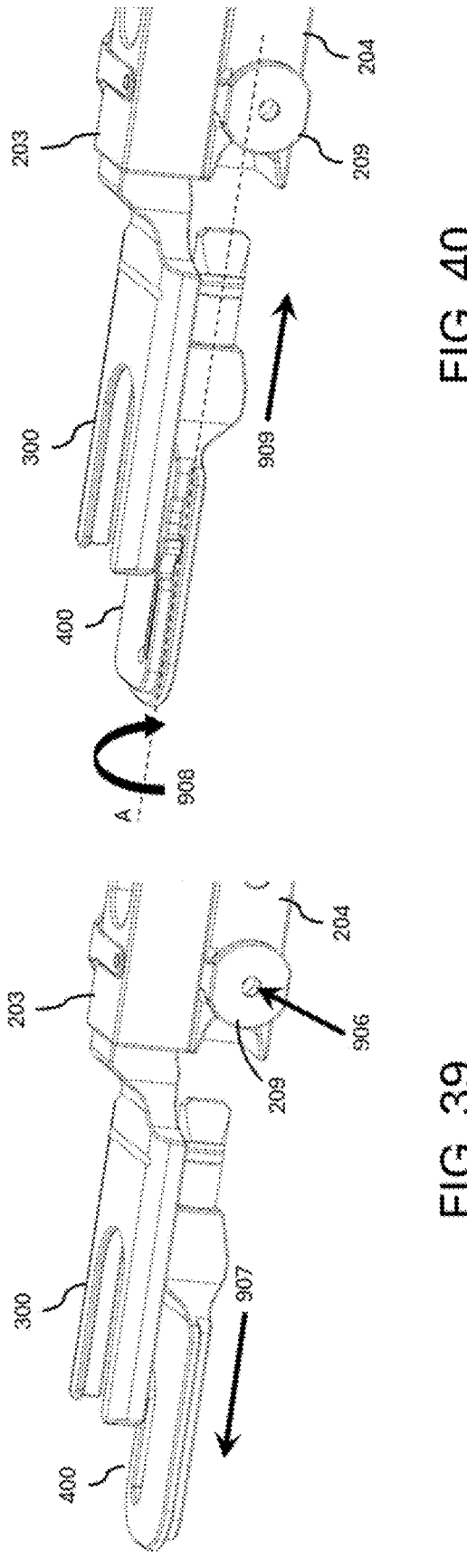
FIG. 39 shows an exemplary step for disassembly of the exemplary distractor system shown in FIG. 1.
FIG. 40 shows an exemplary step for subsequent reassembly of the exemplary distractor system shown in FIG. 1.

With respect to FIGS. 39-40, in this embodiment, the user depresses button 209 using force 906. Detachable tool 400 is removed from distracting member 204 using force 907, rotated about Axis A using rotation 908, and reattached to member 204 using force 909.

Figure 41:
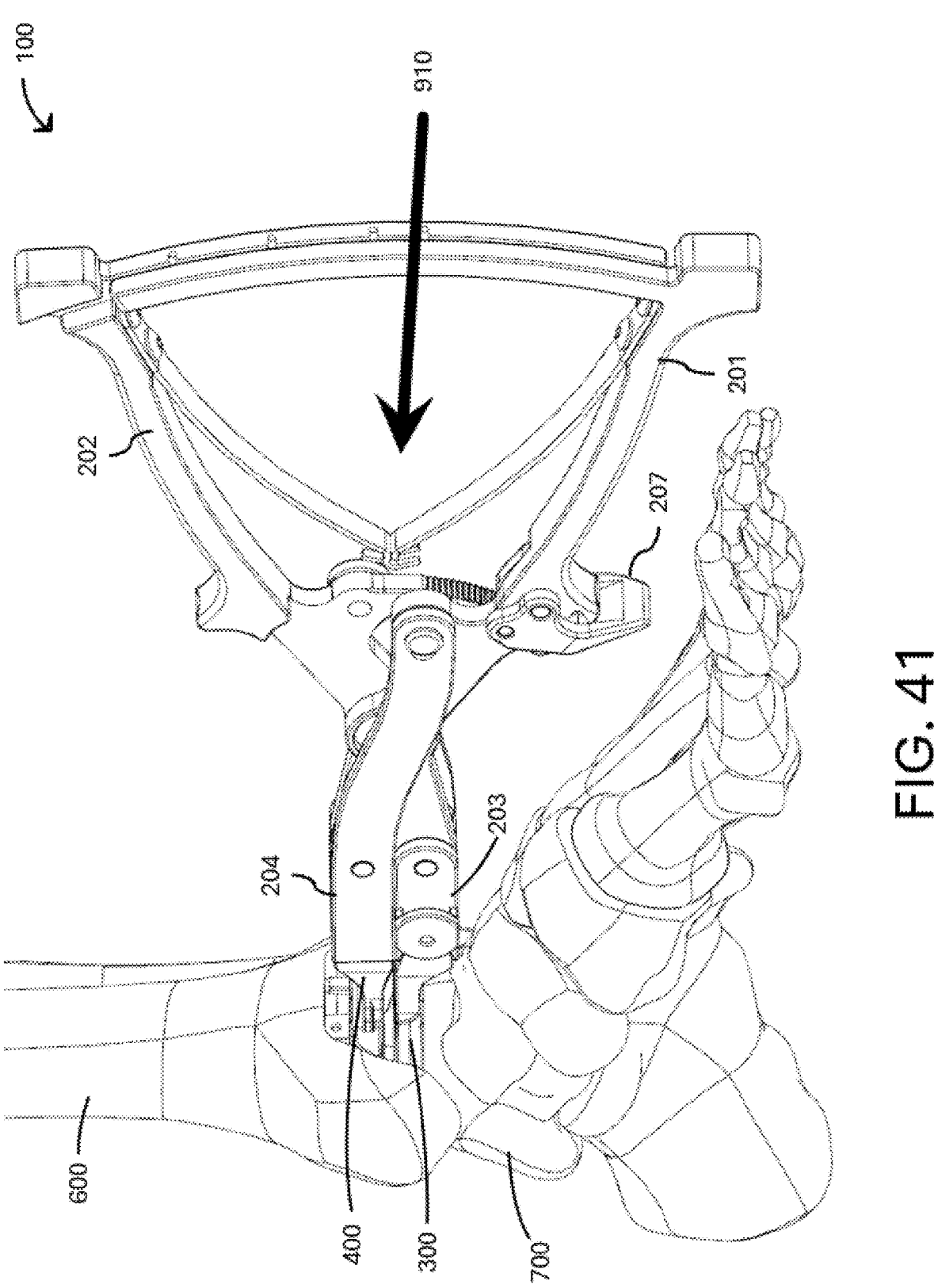
FIG. 41 shows an exemplary subsequent step for use of an exemplary distractor system to further insert the exemplary stemmed implant shown in FIG. 38.
Figure 42:
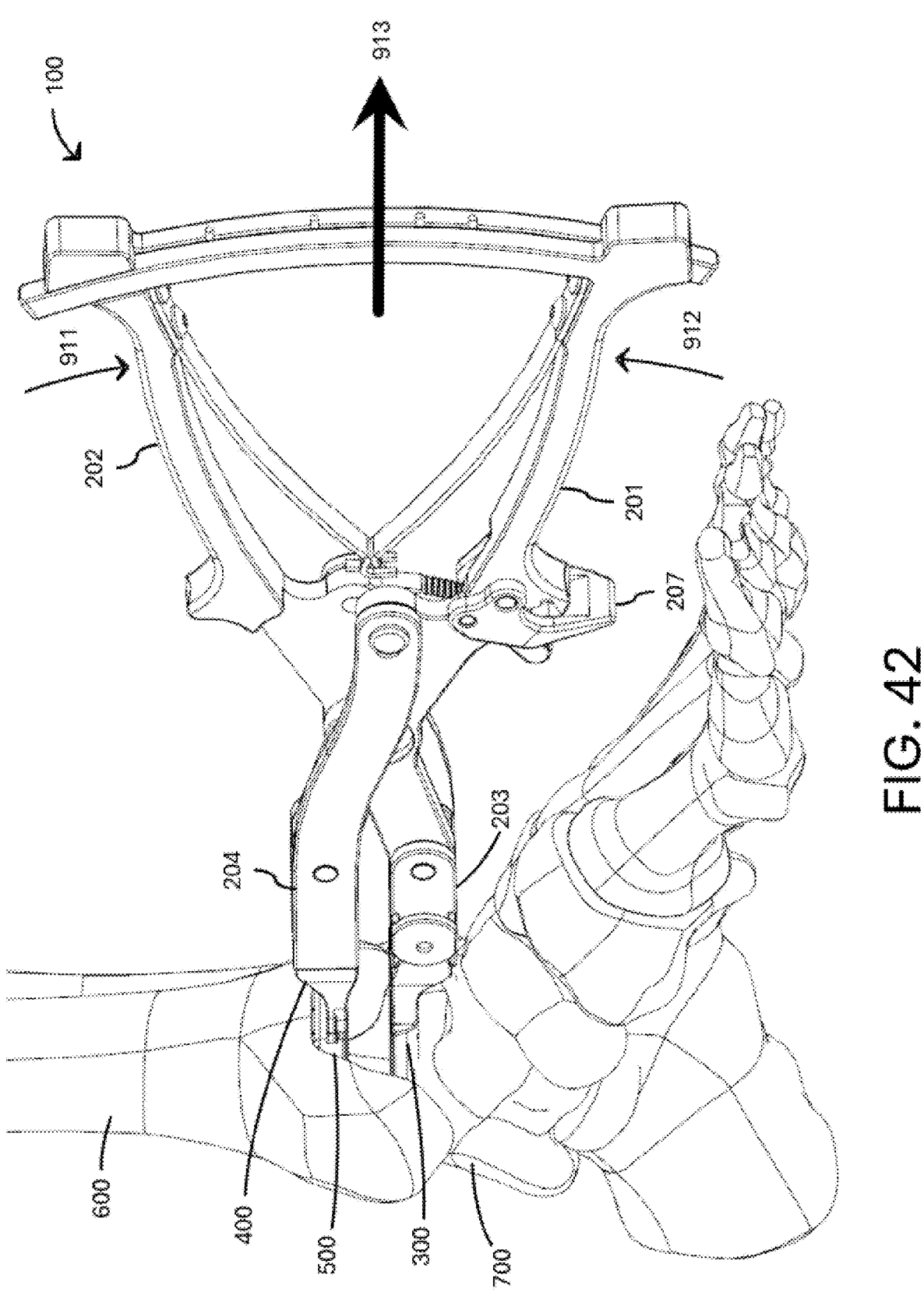
FIG. 42 shows an exemplary subsequent step for use of an exemplary distractor system to further insert the exemplary stemmed implant following the step shown in FIG. 41.

With respect to FIG. 41, in this embodiment, the distractor system 100 is reintroduced to the joint space using force 910 such that detachable tool 400 engages with the stemmed implant 500. As shown in FIG. 41, in this embodiment, the detachable tool 400 is more proximal than detachable tool 300. With respect to FIG. 42, the user applies forces 911 and 912 to the engageable arms 201 and 202 such that the surface 505 of the implant 500 is flush with the bony surface 601. In some embodiments, following use of the distractor system 100 to position the surface 505 of the implant 500 flush with the bony surface 601, the user applies a force 913 to disengage the detachable tool 400 from the stemmed implant 500. In some embodiments the distractor system 100 is used in tandem with an offset impactor to additionally apply an impaction force to seat the implant such that surface 505 is flush with bony surface 601. In some embodiments, the distractor system 100 is replaced with an offset impactor to apply an impaction force to seat the implant such that surface 505 is flush with bony surface 601.

Figures 43, 44:
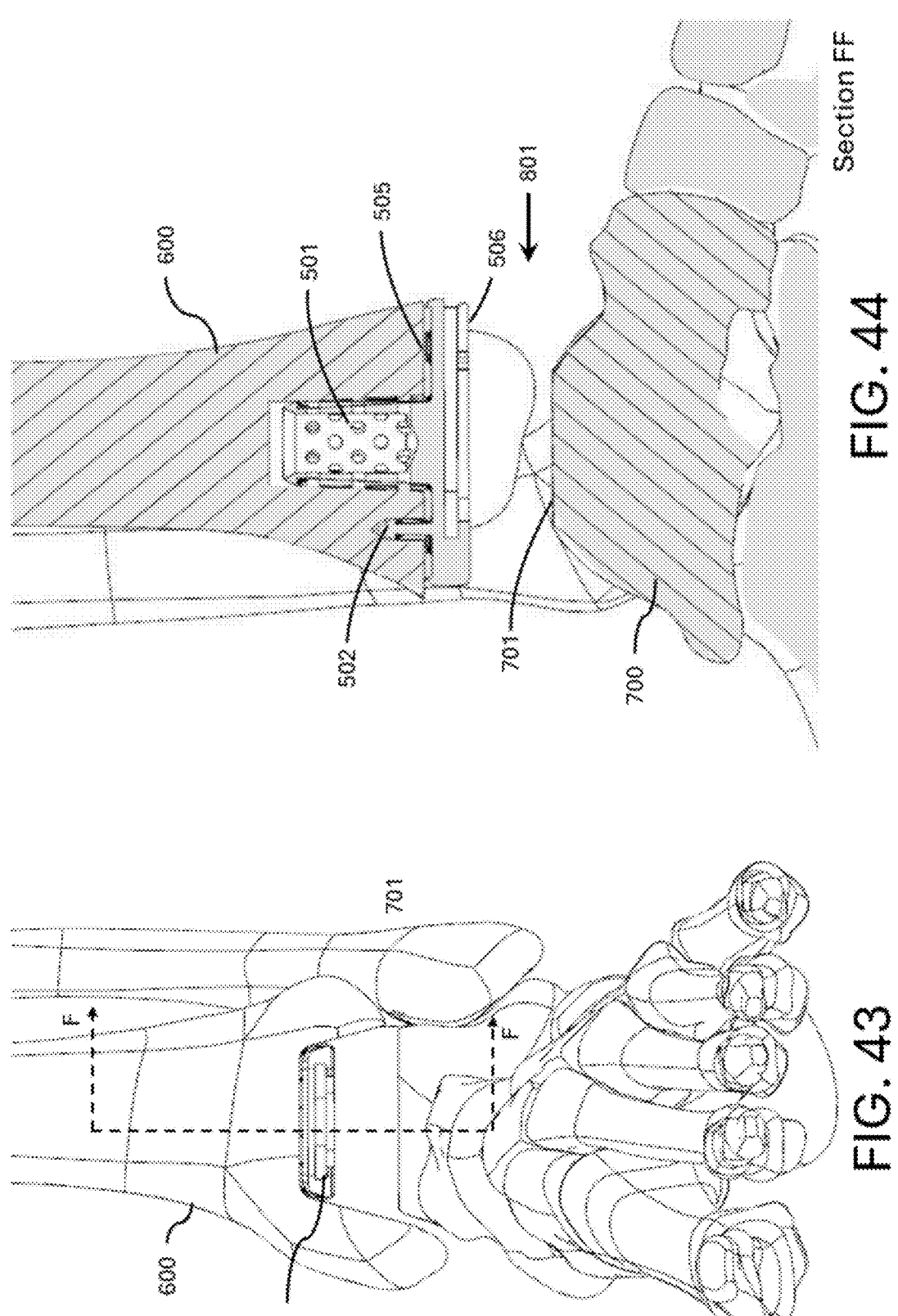
FIG. 43 shows a front view of the exemplary stemmed implant shown in FIG. 27 in its final position following use of the exemplary distractor system shown in FIG. 1.
FIG. 44 shows a section view along section FF shown in FIG. 43.

FIGS. 43 and 44 illustrate various views of the final seated stemmed tibial implant 500. In this embodiment, the joint space 800 is reduced by the distance between surfaces 505 and 506 of implant 500, thereby forming joint space 801. In this embodiment, additional implants for the prepared bony surface 701 may be inserted into space 801. However, it will be appreciated that the joint space 801 may be occupied by the body of implant 500.

In some embodiments, by leveraging a combination of pivotable members, detachable tools, and specialized coupling mechanisms, the exemplary embodiments a versatile and space-efficient solution for TAR procedures. The detachable tools are designed to interface seamlessly with both bony surfaces and implants, ensuring proper alignment and reducing the risk of complications. Additionally, the system's ability to accommodate larger implants addresses the growing demand for patient-specific solutions, leading to improved surgical outcomes and more effective restoration of joint function compared to conventional approaches.

While a number of embodiments of the present invention have been described, it is understood that these embodiments are illustrative only, and not restrictive, and that many modifications may become apparent to those of ordinary skill in the art. For example, all dimensions discussed herein are provided as examples only, and are intended to be illustrative and not restrictive.

What is claimed is:

1. A system, comprising:
    a distractor device, comprising:
        a first engageable arm that is configured to be engaged by a user;
        a second engageable arm that is configured to be engaged by a user,
            wherein the first engageable arm is pivotably connected to the second arm;
        a first distracting member that is coupled to the first engageable arm and to the second engageable arm;
        a second distracting member that is coupled to the first engageable arm and to the second engageable arm;
        wherein the first engageable arm, the second engageable arm, the first distracting member, and the second distracting member are operably coupled to one another such that:
            pivotable motion of the first engageable arm toward the second engageable arm causes the first distracting member and the second distracting member to move away from one another, and
            pivotable motion of the first engageable arm away from the second engageable arm causes the first distracting member and the second distracting member to move toward one another;
    a first tool having a first end, a second end, a planar surface, and a retention mechanism,
        wherein the second end of the first tool is configured to releasably engage a prosthetic device,
        wherein the retention mechanism is configured to retain the second end of the first tool in engagement with the prosthetic device,
        wherein at least one of:
            (a) the planar surface is configured to interface with a first bony surface of two opposing bony surfaces of a joint of a patient, or
            (b) the first tool is configured to position the prosthetic device to interface with the first bony surface, and
        wherein the first end of the first tool is one of (a) configured to be detachably coupled to the second end of the first distracting member, or (b) integrally formed with the second end of the first distracting member; and
    a second tool having a first end, a second end, and a planar surface,
        wherein the planar surface of the second tool is configured to interface with a second bony surface of the two opposing bony surfaces,
        wherein the second tool defines at least one void, wherein the void is sufficiently, shaped, and positioned such that, when (a) the first tool is assembled to the first distracting member, (b) the second tool is assembled to the second distracting member, and (c) the prosthetic device is coupled to the first tool, at least a portion of the prosthetic device passes through the at least one void, and
        wherein the first end of the second tool is one of (a) configured to be detachably coupled to the second end of the second distracting member, or (b) integrally formed with the second end of the second distracting member.

2. The system of claim 1, wherein the distractor device further comprises:
    a transverse arm,
        wherein the transverse arm includes indicators positioned so as to indicate a distance between the first distracting member and the second distracting member, and
        wherein the transverse arm is positioned on one of the first engageable arm or the second engageable arm.

3. The system of claim 2, wherein the indicators comprise one of laser markings or etchings.

4. The system of claim 1, wherein the distractor device further comprises a locking mechanism operable to releasably lock the distractor device,
    wherein, when the distractor device is locked, the first distracting member and the second distracting member are prevented from moving toward one another.

5. The system of claim 4, wherein the locking mechanism comprises a releasable ratcheting mechanism connecting the first engageable arm to the second engageable arm.

6. The system of claim 5, wherein the releasable ratcheting mechanism comprises:
    teeth on one of the first engageable arm or the second engageable arm, and a pawl on an other one of the first engageable arm or the second engageable arm.

7. The system of claim 6, wherein the releasable ratcheting mechanism further comprises:
    a spring-loaded latch operable by a user to release the pawl.

8. The system of claim 1,
    wherein the first end of the first tool is one of configured to be detachably coupled to the second end of the second distracting member,
    wherein the first distracting member comprises a female pocket configured to releasably retain the first tool,
    wherein the first end of the second tool is configured to be detachably coupled to the second end of the second distracting member, and
    wherein the second distracting member comprises a female pocket configured to releasably retain the second tool.

9. The system of claim 8, wherein each of the female pockets comprises:
    a hole configured to receive the first end one of the first tool or the second tool, and
    a biasing member for retaining the first end of the one of the first tool or the second tool within the hole.

10. The system of claim 1,
    wherein the first end of the second tool and the second end of the second tool define a length axis,
    wherein the second tool has a length as measured along the length axis,
    wherein the second tool has a width as measured transverse to the length axis, and wherein the length is greater than the width.

11. The system of claim 10, wherein the void is outlined along the length axis of the second tool leading away from the second end of the second tool.

12. The system of claim 1, wherein the retention mechanism comprises a flexure configured to interface with the prosthetic device.

13. The system of claim 1, wherein the prosthetic device comprises a stemmed tibial implant for a total ankle replacement.

14. A method, comprising:

forming an anterior resection of a first bone of a joint of a patient to form a space between the first bone and a second bone of the joint;

forming a stem hole in a distal end of the first bone;

attaching a first tool to a first distracting member of a distractor device, wherein the distractor device comprises:

a first engageable arm that is configured to be engaged by a user;

a second engageable arm that is configured to be engaged by a user, wherein the first engageable arm is pivotably connected to the second arm;

a first distracting member that is coupled to the first engageable arm and to the second engageable arm;

a second distracting member that is coupled to the first engageable arm and to the second engageable arm;

wherein the first engageable arm, the second engageable arm, the first distracting member, and the second distracting member are operably coupled to one another such that:

pivotable motion of the first engageable arm toward the second engageable arm causes the first distracting member and the second distracting member to move away from one another, and pivotable motion of the first engageable arm away from the second engageable arm causes the first distracting member and the second distracting member to move toward one another;

wherein the first tool has a first end, a second end, a planar surface, and a retention mechanism, wherein the second end of the first tool is configured to releasably engage a prosthetic device, wherein the retention mechanism is configured to retain the second end of the first tool in engagement with the prosthetic device, wherein at least one of:

(a) the planar surface is configured to interface with a first bony surface of two opposing bony surfaces of a joint of a patient, or (b) the first tool is configured to position the prosthetic device to interface with the first bony surface, and wherein the first end of the first tool is one of (a) configured to be detachably coupled to the second end of the first distracting member, or (b) integrally formed with the second end of the first distracting member;

attaching a second tool to the second distracting member of the distraction device, wherein the second tool has a first end, a second end, and a planar surface, wherein the planar surface of the second tool is configured to interface with a second bony surface of the two opposing bony surfaces, wherein the second tool defines at least one void, wherein the void is sufficiently, shaped, and positioned such that, when (a) the first tool is assembled to the first distracting member, (b) the second tool is assembled to the second distracting member, and (c) the prosthetic device is coupled to the first tool, at least a portion of the prosthetic device passes through the at least one void, and wherein the first end of the second tool is one of (a) configured to be detachably coupled to the second end of the second distracting member, or (b) integrally formed with the second end of the second distracting member;

attaching a prosthetic device to the first tool, wherein the prosthetic device comprises a stem;

inserting the distraction device into the space;

operating the distraction device to increase a distance between the first bone and the second bone;

inserting the distraction device further into the space to align the stem of the prosthetic device with the stem hole; and operating the distraction device to decrease the distance between the first bone and the second bone, so as to result in the stem of the prosthetic device passing through the void of the second tool and into the stem hole.

15. The method of claim 14, wherein the step of forming the stem hole is performed using a cutting bit.

16. The method of claim 14, further comprising:

forming peripheral holes around the stem hole using a cutting pin.

17. The method of claim 16, wherein the prosthetic device includes peripheral fixation pegs positioned around the stem, and wherein the step of operating the distraction device to decrease the distance between the first bone and the second bone also results in the peripheral fixation pegs passing into the peripheral holes.

18. The method of claim 17, further comprising:

impacting the prosthetic device so as to fix the stem in the stem hole and so as to fix the peripheral fixation pegs in the peripheral holes.

19. The method of claim 18, wherein the step of impacting the prosthetic device is performed using an offset impactor.

20. The method of claim 14, wherein the stem comprises a conical cage.

* * * * *